US012674192B2

(12) United States Patent (10) Patent No.: US 12,674,192 B2

Fujioka et al. (45) Date of Patent: *Jul. 7, 2026

(54) ADAPTER MOLECULE, BIOMOLECULE-ADAPTER MOLECULE COMPLEX IN WHICH SAID ADAPTER MOLECULE AND BIOMOLECULE ARE BOUND, BIOMOLECULE ANALYSIS APPARATUS, AND BIOMOLECULE ANALYSIS METHOD

(71) Applicant: Hitachi High-Tech Corporation, Tokyo (JP)

(72) Inventors: Michiru Fujioka, Tokyo (JP); Yusuke Goto, Tokyo (JP); Rena Akahori, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 1106 days.

This patent is subject to a terminal disclaimer.

(21) Appl. No.: 17/642,887

(22) PCT Filed: Sep. 18, 2019

(86) PCT No.: PCT/JP2019/036511

§ 371 (c)(1),
(2) Date: Mar. 14, 2022

(87) PCT Pub. No.: WO2021/053744

PCT Pub. Date: Mar. 25, 2021

(65) Prior Publication Data

US 2022/0396829 A1      Dec. 15, 2022

(51) Int. Cl.
*C12Q 1/6832*      (2018.01)
*C12N 15/11*      (2006.01)
*C12Q 1/6809*      (2018.01)
*C12Q 1/6816*      (2018.01)
*C12Q 1/6874*      (2018.01)
*C12Q 1/6876*      (2018.01)

(52) U.S. Cl.
CPC ........... *C12Q 1/6832* (2013.01); *C12N 15/11* (2013.01); *C12Q 1/6809* (2013.01); *C12Q 1/6816* (2013.01); *C12Q 1/6874* (2013.01); *C12Q 1/6876* (2013.01)

(58) Field of Classification Search
CPC .. C12Q 1/6832; C12Q 1/6809; C12Q 1/6816; C12Q 1/6874; C12Q 1/6876; C12Q 1/6869; C12N 15/11; C12M 1/00
See application file for complete search history.

(56) References Cited

U.S. PATENT DOCUMENTS

| | | | |
|---|---|---|---|
| 9,017,937 B1 | 4/2015 | Turner et al. | |
| 10,365,287 B2 | 7/2019 | Sakai et al. | |
| 10,662,471 B2 | 5/2020 | Davis et al. | |
| 2010/0035260 A1 | 2/2010 | Olasagasti et al. | |
| 2017/0107569 A1* | 4/2017 | Heron ................. | C12Q 1/6869 |
| 2018/0030506 A1 | 2/2018 | Fujioka | |
| 2018/0223351 A1 | 8/2018 | Davis et al. | |
| 2019/0078145 A1 | 3/2019 | Hong et al. | |
| 2020/0308641 A1* | 10/2020 | Davis .................. | C12Q 1/6869 |

FOREIGN PATENT DOCUMENTS

| | | | | |
|---|---|---|---|---|
| CN | 104254771 A | 12/2014 | | |
| CN | 107208162 A | 9/2017 | | |
| DE | 112015005465 T5 * | 8/2017 | .......... | C12Q 1/6869 |
| JP | 2010-230614 A | 10/2010 | | |
| JP | 5372570 B2 | 12/2013 | | |
| JP | 2015-505458 A | 2/2015 | | |
| JP | 2017-503517 A | 2/2017 | | |
| WO | WO 2013/109970 A1 | 7/2013 | | |
| WO | WO 2015/110813 A1 | 7/2015 | | |

OTHER PUBLICATIONS

Rena et al., DE-112015005465-T5, translated document, Aug. 17, 2017.*

Chinese-language Office Action issued in Chinese Application No. 201980100366.7 dated May 4, 2023 (7 pages).

Chinese-language Office Action issued in Chinese Application No. 201980100366.7 dated Jan. 22, 2024 with English translation (8 pages).

International Search Report (PCT/ISA/210) issued in PCT Application No. PCT/JP2019/036511 dated Dec. 3, 2019 with English translation (four (4) pages).

Japanese-language Written Opinion (PCT/ISA/237) issued in PCT Application No. PCT/JP2019/036511 dated Dec. 3, 2019 (six (6) pages).

Cherf G. et al., "Automated forward and reverse ratcheting of DNA in a nanopore at 5-Å precision", Nature Biotechnology, Apr. 2012, pp. 344-348, vol. 30, No. 4 (five pages).

Great Britain Office Action issued in Great Britain Application No. GB2203248.6 dated Jun. 21, 2024 (4 pages).

* cited by examiner

*Primary Examiner* — Cynthia B Wilder

(74) *Attorney, Agent, or Firm* — Crowell & Moring LLP

(57)      ABSTRACT

A double-stranded DNA to be analyzed is analyzed without subjecting it to a modification treatment. An adapter molecule to be bound to the double-stranded DNA to be analyzed has a double-stranded nucleic acid region having base sequences complementary to each other, a pair of single-stranded nucleic acid regions having base sequences non-complementary to each other, and a block molecule placed in one of the single-stranded nucleic acid regions.

9 Claims, 20 Drawing Sheets

Specification includes a Sequence Listing.

FIG. 10

1. ADAPTOR HYBRIDIZATION:
    80 °C 10 min → 30 °C 30 min

| HOMOADAPTOR-TEMPLATE 10 uM | 1 uL |
|---|---|
| HOMOADAPTOR-PRIMER 10 uM | 1 uL |
| 10x ISOTHERML BUFFER II | 1 uL |
| D.W. | 7 uL |
| TOTAL | 10 uL |

2. END REPAIR/ dA TAILING:
    20 °C 30 min → 65 °C 30 min → 4 °C
    → AMPure PURIFICATION

| DNA SAMPLE 500 ng/uL | 2 uL |
|---|---|
| 1x TE BUFFER | 48 uL |
| ULTRA II END REPAIR BUFFER | 7 uL |
| ULTRA II END REPAIR ENZYME | 3 uL |
| TOTAL | 60 uL |

3. LIGATION:
    R.T. 30 min → ON ICE
    → AMPure PURIFICATION

| (1) HYBRIDIZED ADAPTOR 0.5 uM | 20 uL |
|---|---|
| (2) dA TAILING DNA SAMPLES | 20 uL |
| BLUNT/ TA LIGASE MASTERMIX | 40 uL |
| TOTAL | 80 uL |

4. PRIMER HYBRIDIZATION:
    30 °C 30 min

| (3) PURIFIED LIGATED DNA SAMPLES | 20 uL |
|---|---|
| SEQUENCINGOLIGO 1 uM | 2.5 uL |
| 10x ISOTHERML BUFFER II | 2.5 uL |
| TOTAL | 25 uL |

ADAPTER MOLECULE, BIOMOLECULE-ADAPTER MOLECULE COMPLEX IN WHICH SAID ADAPTER MOLECULE AND BIOMOLECULE ARE BOUND, BIOMOLECULE ANALYSIS APPARATUS, AND BIOMOLECULE ANALYSIS METHOD

TECHNICAL FIELD

The present invention relates to an adapter molecule used for the analysis of a biomolecule such as a nucleic acid, a biomolecule to which the adapter molecule is bound, a biomolecule analysis apparatus, and a method of analyzing a biomolecule.

BACKGROUND ART

Biomolecules such as proteins or nucleic acid molecules each have a structure in which monomers such as amino acids or nucleotides are linked to each other, respectively. The monomer sequence of a protein, among these biomolecules, is determined using an apparatus in which the Edman method is performed in an automated manner (which apparatus is called "peptide sequencer" or "protein sequencer"). As an apparatus for determining the monomer sequence (base sequence) of a nucleic acid molecule, there are known a first-generation sequencer using the Sanger's method or the Maxam-Gilbert sequencing and a second-generation sequencer using the pyrosequencing method or a method using the bridge PCR method and the single base synthesis (sequence-by-synthesis, SBS) technique in combination.

In addition, different from the aforesaid various sequencers, a method of directly and electrically measuring the monomer sequence of a biomolecule without conducting an elongation reaction or fluorescence labeling has attracted attentions in the field of a next-generation sequencer. Described specifically, this method includes passing a biomolecule having the aforesaid monomer sequence structure through a nanoscale hole, detecting an electric signal generated at this time, and determining the monomer sequence based on the change of the electric signal. More specifically, active research and development of a nanopore DNA sequencing system for a nucleic acid molecule are currently underway and some systems have already been industrialized.

In this nanopore DNA sequencing system, a base sequence is determined by measuring a block current generated when a DNA strand passes through a small pore (which will hereinafter be called "nanopore") formed in a thin film. This means that since a block current changes, depending on the kind of individual bases contained in a DNA strand, the kind of the base can be identified successively by measuring the amount of the block current. Different from the aforesaid various sequencers, this system requires neither an amplification reaction by an enzyme having a DNA strand as a template nor addition of a labeling substance such as phosphor. In comparison to conventional various sequencers, the nanopore DNA sequencing system has a high throughput, needs a low running cost, and enables decoding of a long-base DNA.

This nanopore DNA sequencing system is generally realized by a biomolecule analysis device equipped with first and second liquid tanks filled with an electrolyte solution, a thin film which divides the first liquid tank from the second liquid tank and has nanopores, and first and second electrodes provided in the first and second liquid tanks. The biomolecule analysis device can be constituted as an array device. The array device is a device having a plurality of combinations of liquid chambers divided by a thin film. For example, it has a first liquid tank as a common tank and a second tank comprised of a plurality of individual tanks. In this case, an electrode is placed in each of the common tank and the individual tanks.

In the aforesaid structure, a voltage is applied to between the first liquid tank and the second liquid tank and at the same time, an ionic current depending on the diameter of a nanopore flows through the nanopore. A potential gradient depending on an applied voltage is formed across the nanopore. When a biomolecule is introduced into the first liquid tank, the biomolecule is sent to the second liquid tank via the nanopore, depending on the diffusion phenomenon and the potential gradient thus generated. The amount of the ionic current is proportional to the cross-sectional area of the nanopore as first approximation. When the DNA passes through the nanopore, it blocks the nanopore and decreases the effective cross-sectional area, so that the ionic current decreases. This current is called "block current". Based on the amount of the block current, a difference between the single strand and double strand of DNA or the kind of the base is judged.

Another system also known includes providing a pair of probe electrodes opposite to each other on inner side surface or the like of a nanopore, applying a voltage to between the electrodes, and thereby measuring a tunnel current between the DNA and the probe electrodes when it passes through the nanopore and determining the kind of the base from the amount of the tunnel current.

One of the problems of the nanopore DNA sequencing system is the transfer control of DNA passing through a nanopore. To determine the difference among individual bases contained in a DNA strand by a block current amount, it is thought that the nanopore passage speed of DNA should be controlled to 100 μs or more per base in consideration of the current noise and the time constant of the fluctuations in a DNA molecule during the measurement. However, the passage speed of DNA through a nanopore is usually as fast as 1 μs or less per base, making it difficult to sufficiently measure the block current derived from each base.

One of the transfer control methods is to make use of the feed control power of a single-stranded DNA serving as a template when a DNA polymerase mediates a complementary strand synthesis reaction or when helicase unwinds a double-stranded DNA (refer to, for example, Nonpatent Literature 1). A DNA polymerase binds to a template DNA and starts a complementary strand synthesis reaction from the terminal portion of a primer which complementarily binds to the template DNA. A DNA polymerase conducts a complementary strand synthesis reaction in the vicinity of a nanopore in the first liquid tank, so that the template DNA is transferred to the second liquid tank via the nanopore. Such a DNA polymerase or helicase is called "a molecular motor".

As described in Patent Literature 1, the measurement accuracy can be improved by reciprocating a single-stranded DNA to be analyzed between the first liquid tank and the second liquid tank via a nanopore. This means that by reciprocating a single-stranded DNA to be analyzed between the first liquid tank and the second liquid tank and thereby measuring a plurality of times, an error which has occurred by a single measurement can be corrected. As described in Patent Literature 1, after a first stopper molecule (larger than the diameter of a nanopore) is bound to one of the terminal portions of the single-stranded DNA to be analyzed and the single-stranded DNA is transferred from the other terminal portion of the single-stranded DNA via a nanopore to the second liquid tank, a second stopper molecule (larger than the diameter of the nanopore) is bound to the other terminal portion of the single-stranded DNA in the second liquid tank. This makes it possible to leave the one terminal portion of the single-stranded DNA in the first liquid tank, leave the other terminal portion in the second liquid tank, and thereby prevent the single-stranded DNA from falling from the nanopore during the reciprocating movement.

CITATION LIST

Nonpatent Literature 1: Gerald M Cherf et al., Nat. Biotechnol. 30, No. 4, pp. 344-348, 2012
Patent Literature 1: Japanese Patent No. 5372570

SUMMARY OF INVENTION

Technical Problem

In the nanopore DNA sequencing system disclosed in Patent Literature 1, a double-stranded DNA to be analyzed is caused to pass through a nanopore after modified into a single-stranded DNA. This means that conventionally, the nanopore DNA sequencing system requires a treatment for modifying a double-stranded DNA to be analyzed into a single-stranded DNA. The nanopore DNA sequencing system needs time or cost for the aforesaid treatment and is therefore cumbersome.

Also the system disclosed in Nonpatent Literature 1 or the like has a problem similar to that of the nanopore DNA sequencing system disclosed in Patent Literature 1, because a nucleic acid to be analyzed is a single-stranded DNA and analysis of a double-stranded DNA requires a modification treatment.

With the aforesaid circumstances in view, a purpose of the present invention is to provide an adapter molecule, a biomolecule-adapter molecule complex in which the aforesaid adapter molecule is bound to a biomolecule, a biomolecule analysis apparatus, and a biomolecule analysis method, each capable of avoiding a cumbersome treatment such as the modification of a double-stranded DNA to be analyzed.

Solution to Problem

The present inventors have conducted keen researches to achieve the aforesaid purpose. As a result, it has been found that by designing an adapter molecule having a single-stranded region capable of passing through a nanopore and linking the adapter molecule to a biomolecule to be analyzed, a modification treatment of the double-stranded DNA becomes unnecessary, leading to the completion of the present invention.

The present invention includes the following.
(1) An adapter molecule including:
a double-stranded nucleic acid region having one terminal portion which directly or indirectly binds to a biomolecule to be analyzed and having base sequences complementary to each other,
a pair of single-stranded nucleic acid regions linked to the other terminal portion different from the one terminal portion in the double-stranded nucleic acid region and having base sequences non-complementary to each other, and a block molecule placed in one single-stranded nucleic acid region of the aforesaid pair of single-stranded nucleic acid regions and having a diameter larger than the diameter of a nanopore in an analysis apparatus of the biomolecule.
(2) The adapter molecule as described in (1), wherein the block molecule is placed in a single-stranded nucleic acid region which is one of the pair of single-stranded nucleic acid regions and has a 3' end as a terminal portion thereof.
(3) The adapter molecule as described in (1), wherein the block molecule is a molecule which can bind to the single-stranded nucleic acid region or has a hairpin structure formed in a complementary region in the single-stranded nucleic acid region.
(4) The adapter molecule as described in (1), wherein a single-stranded nucleic acid region which is one of the pair of single-stranded nucleic acid regions and has a 3' end as a terminal portion thereof is equipped with a molecular motor binding site to which a molecular motor is bound.
(5) The adapter molecule as described in (4), wherein the single-stranded nucleic acid region equipped with the molecular motor binding site has, on the side of the 3' end relative to the molecular motor binding site, a primer binding site with which a primer is hybridized.
(6) The adapter molecule as described in (5), wherein the molecular motor binding site and the primer binding site have therebetween a spacer to which the molecular motor is not bound.
(7) The adapter molecule as described in (1), wherein a single-stranded nucleic acid region which is one of the pair of single-stranded nucleic acid regions and has a 5' end as a terminal portion thereof has thymine as up to at least the 2nd base from the 5' end.
(8) The adapter molecule as described in (1), wherein the double-stranded nucleic acid region has a labeling sequence.
(9) A bio-adapter molecule complex having a biomolecule to be analyzed and the adapter molecule as described above in any of (1) to (8) bounded directly or indirectly to each end of the biomolecule.
(10) The bio-adapter molecule complex as described in (9), wherein the biomolecule to be analyzed is a double-stranded nucleic acid.
(11) A biomolecule analysis apparatus including:
a thin film having a nanopore,
a first liquid tank and a second liquid tank placed opposite to each other via the thin film,
a voltage source for applying a voltage to between the first liquid tank and the second liquid tank while filling the first liquid tank with an electrolyte solution containing the bio-adapter molecule complex described in (9) or (10) and filling the second liquid tank with an electrolyte solution, and
a controller for controlling the voltage source to form a desired potential gradient between the first liquid tank and the second liquid tank.
(12) A method of analyzing a biomolecule, including:
a step of applying a voltage to between a first liquid tank and a second liquid tank, which are placed opposite to each other via a thin film having a nanopore, while filling the first liquid tank with an electrolyte solution containing the bio-adapter molecule complex described in (9) or (10) and filling the second liquid tank with an electrolyte solution to form a potential gradient with the first liquid tank as a negative or ground potential and with the second liquid tank as a positive potential, and a step of measuring a signal generated when the bio-adapter molecule complex passes through the nanopore from the second liquid tank to the first liquid tank;

wherein in the step of forming a potential gradient, a single-stranded nucleic acid region of the bio-adapter molecule complex is introduced into the second liquid tank via the nanopore and the bio-adapter molecule complex transfers from the first liquid tank to the second liquid tank by the potential gradient.

(13) The method of analyzing a biomolecule as described in (12), wherein the bio-adapter molecule complex has the block molecule placed in a single-stranded nucleic acid region having a 3' end as a terminal portion thereof, a single-stranded nucleic acid region having a 5' end as a terminal portion thereof is introduced into the second liquid tank via the nanopore, the bio-adapter molecule complex is transferred from the first liquid tank to the second liquid tank by a potential gradient, and the block molecule placed in the single-stranded nucleic acid region having a 3' end as a terminal portion thereof is brought into contact with the nanopore to stop the transfer of the bio-adapter molecule complex from the first liquid tank to the second liquid tank.

(14) The method of analyzing a biomolecule as described in (12), wherein the bio-adapter molecule complex has a molecular motor binding site placed in a single-stranded nucleic acid region having a 3' end as a terminal portion thereof, the electrolyte solution with which the first liquid tank is filled contains a molecular motor which binds to the molecular motor binding site, and the molecular motor binds to the molecular motor binding site and transfers the bio-adapter molecule complex from the second liquid tank to the first liquid tank.

(15) The method of analyzing a biomolecule as described in (12), wherein the bio-adapter molecule complex has a molecular motor binding site in a single-stranded nucleic acid region having a 3' end as a terminal portion thereof and has a primer binding site on the side of the 3' end relative to the molecular motor binding site;

the electrolyte solution with which the first liquid tank is filled contains a molecular motor which can be bound to the molecular motor binding site and a primer which can be hybridized with the primer binding site, and the molecular motor synthesizes a complementary strand from the primer hybridized with the primer binding site and thereby transfers the bio-adapter molecule complex from the second liquid tank to the first liquid tank.

(16) The method of analyzing a biomolecule as described in (12), wherein the bio-adapter molecule complex has a molecular motor binding site in a single-stranded nucleic acid region having a 3' end as a terminal portion thereof, a primer binding site on the side of the 3' end relative to the molecular motor binding site, and a spacer to which the molecular motor cannot be bound between the molecular motor binding site and the primer binding site, the electrolyte solution with which the first liquid tank is filled contains a molecular motor which can be bound to the molecular motor binding site and a primer which can be hybridized with the primer binding site, and the molecular motor in contact with the nanopore synthesizes a complementary strand from the primer hybridized with the primer binding site and thereby transfers the bio-adapter molecule complex from the second liquid tank to the first liquid tank.

(17) The method of analyzing a biomolecule as described in (12), wherein in the step of measuring a signal, a voltage applied to between the first liquid tank and the second liquid tank is reversed when a signal from a specific region of the adapter molecule is measured and a potential gradient is formed with the first liquid tank as a positive potential and with the second liquid tank as a negative or ground potential.

(18) The method of analyzing a biomolecule as described in (12), wherein the electrolyte solution with which the second liquid tank is filled contains a molecule which can bind to a 5' end of a single-stranded nucleic acid region of the bio-adapter molecule complex, and the molecule binds to the 5' end of the single-stranded nucleic acid region introduced into the second liquid tank via the nanopore.

(19) The method of analyzing a biomolecule as described in (12), wherein the step of measuring a signal is repeated by controlling a voltage to be applied to between the first liquid tank and the second liquid tank and thereby reciprocating the bio-adapter molecule complex between the first liquid tank and the second liquid tank.

Advantageous Effects of Invention

The adapter molecule according to the present invention has a pair of single-stranded nucleic acid regions having, at a terminal portion thereof, base sequences non-complementary to each other while directly or indirectly binding to a biomolecule to be analyzed. By introducing the single-stranded nucleic acid region in a nanopore, the biomolecule to be analyzed can be guided into the nanopore easily. When the biomolecule to be analyzed is a double-stranded nucleic acid, the double-stranded nucleic acid is easily detached (Unziped) into a single-stranded nucleic acid by passing through the nanopore with the single-strand nucleic acid region first.

In the bio-adapter molecule complex of the present invention, the adapter molecule directly or indirectly binds to a biomolecule to be analyzed and has, at a terminal portion thereof, a pair of single-stranded nucleic acid regions respectively having base sequences non-complementary to each other. This single-stranded nucleic acid region can be introduced into the nanopore. When the biomolecule to be analyzed is a double-stranded nucleic acid, the double-stranded nucleic acid can easily be detached (Unziped) into a single-stranded nucleic acid by passing through the nanopore with the single-stranded nucleic acid region first.

The method of analyzing a biomolecule according to the present invention introduces a single-stranded nucleic acid region of the bio-adapter molecule complex in a nanopore and transfers the bio-adapter molecule complex from the first liquid tank to the second liquid tank by making use of a potential gradient between the first liquid tank and the second liquid tank. When the biomolecule to be analyzed is a double-stranded nucleic acid, the double-stranded nucleic acid is easily detached (Unziped) into a single-stranded nucleic acid by passing through the nanopore with the single-strand nucleic acid region first.

BRIEF DESCRIPTION OF DRAWINGS

FIG. 10 is a diagram showing the composition of a reaction liquid and reaction conditions in various reactions conducted in the present example.

DESCRIPTION OF EMBODIMENTS

The adapter molecule, bio-adapter molecule complex, and method of analyzing a biomolecule according to the present invention will hereinafter be described specifically with reference to drawings. However, the drawings show specific embodiments based on the principle of the present invention, are for facilitating the understanding of the present invention, and are not used for limited interpretation of the present invention.

First Embodiment

Figure 1:
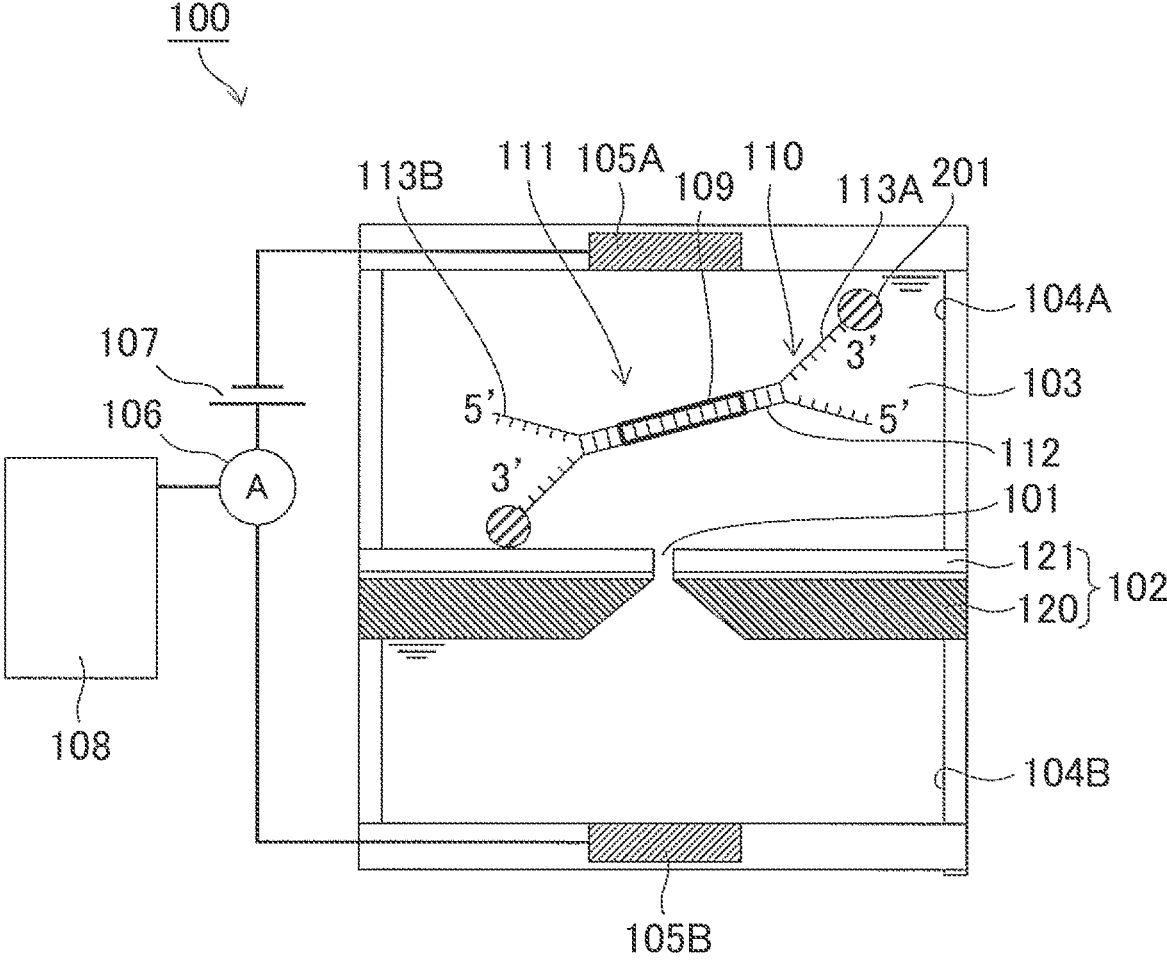
FIG. 1 is a block diagram schematically showing a biomolecule analysis apparatus to which the present invention is applied.

FIG. 1 shows an example of the structure of a biomolecule analysis apparatus for analyzing a bio-adapter molecule complex in which an adapter molecule and a biomolecule to be analyzed are directly or indirectly linked to each other. The biomolecule analysis apparatus shown in FIG. 1 is a biomolecule analyzing device for measuring an ionic current by a block current system. It is equipped with a substrate 102 having a nanopore 101 formed therein, a pair of liquid tanks 104 (a first liquid tank 104A and a second liquid tank 104B) placed adjacent to the substrate 102 with the substrate therebetween and filled with an electrolyte solution 103, and a pair of electrodes 105 (a first electrode 105A and a second electrode 105B) adjacent to the first liquid tank 104A and the second liquid tank 104B, respectively. During measurement, a predetermined voltage is applied to between the pair of electrodes 105 from a voltage source 107 and an electric current flows between the pair of electrodes 105. The amount of the current flowing between the electrodes 105 is measured by an ammeter 106 and the value thus measured is analyzed by a computer 108.

For the electrolyte solution 103, for example, KCl, NaCl, LiCl, or CsCl is used. The respective electrolyte solutions 103 in the first liquid tank 104A and the second liquid tank 104B may have the same composition or different compositions. It is to be noted that the first liquid tank 104A is filled with an electrolyte solution 103 containing a bio-adapter molecule complex which will be described in detail later. The electrolyte solution 103 in the second liquid tank 104B may also contain 4M or more Urea or DMSO, DMF, or NaOH to suppress the biomolecule from forming a self-complementary strand. It may also contain a buffer to stabilize the biomolecule. Examples of the buffer include Tris, EDTA, and PBS. The first electrode 105A and the second electrode 105B may be prepared from, for example, a material having conductivity such as Ag, AgCl, or Pt.

Figure 2:
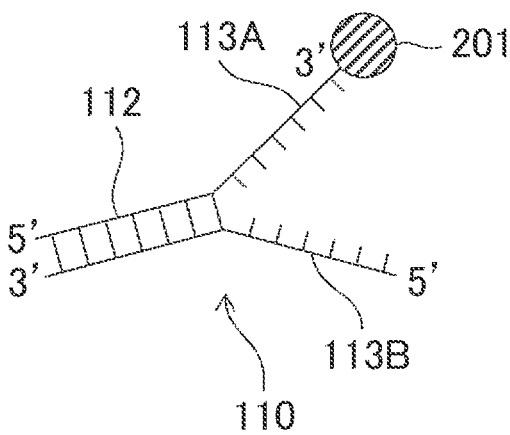
FIG. 2 is a block diagram schematically showing an adapter molecule according to a first embodiment.

The electrolyte solution 103 with which the first liquid tank 104A is filled contains a bio-adapter molecule complex 111 containing a biomolecule 109 (double-stranded DNA, etc.) to be analyzed and an adapter molecule 110. The adapter molecule 110 has, as shown in FIG. 2, a double-stranded nucleic acid region 112 which directly binds to the biomolecule 109, a pair of single-stranded nucleic acid regions 113A and 113B linked to a terminal portion of the double-stranded nucleic acid region 112 different from that bound to the biomolecule 109 and respectively having base sequences non-complementary to each other, and a block molecule 201 placed at one of the ends of the single-stranded nucleic acid regions 113A and 113B. It is to be noted that the single-stranded nucleic acid region 113A has a 3' end and the single-stranded nucleic acid region 113B has a 5' end. In the example shown in FIG. 2, the block molecule 201 is placed at the terminal portion of the single-stranded nucleic acid region 113A having a 3' end. The block molecule 201 may be placed not at the terminal portion of the single-stranded nucleic acid region 113A but at the terminal portion of the single-stranded nucleic acid region 113B having a 5' end.

After addition of the biomolecule 109, the adapter molecule 110, and a DNA ligase to the electrolyte solution 103 with which the first liquid tank 104A is filled, the bio-adapter molecule complex 111 may be prepared in the resulting electrolyte solution 103 with which the first liquid tank 104A is filled.

Although not shown, indirect linking of the adapter molecule 110 and the biomolecule 109 is possible. The term "indirect linking" embraces linking of the adapter molecule 110 and the biomolecule 109 via a nucleic acid fragment having a predetermined base length or linking of the adapter molecule 110 and the biomolecule 109 via a functional group to be introduced depending on the kind of the biomolecule 109.

Further, in the adapter molecule 110, the terminal portion of the double-stranded nucleic acid region 112 to be linked to the biomolecule 109 is preferably a 3' protruding end (for example, dT protruding end). When the terminal portion is a 3'dA protruding end, the adapter molecule 110 can be prevented from forming a dimer when the adapter molecule 110 is linked to the biomolecule 109.

Further, in the adapter molecule 110, the length and base sequence of the double-stranded nucleic acid region 112 are not particularly limited and they may be any length and any base sequence. For example, the double-stranded nucleic acid region 112 may have a length of 5 to 100 bases, 10 to 80 bases, 15 to 60 bases, and 20 to 40 bases.

Further, in the adapter molecule 110, the length and the base sequence of the single-stranded nucleic acid regions 113A and 113B are not particularly limited and they may be any length and any base sequence. The single-stranded nucleic acid regions 113A and 113B may have the same length or different lengths, respectively. The single-stranded nucleic acid regions 113A and 113B may have base sequences in common or may have completely different base sequences as long as they are non-complementary to each other. The term "non-complementary" means that in the entire base sequence of the single-stranded nucleic acid regions 113A and 113B, 30% or less, preferably 20% or less, more preferably 10% or less, still more preferably 5% or less, most preferably 3% or less of the base sequence is a complementary one.

The single-stranded nucleic acid regions 113A and 113B may have, for example, a length of 10 to 200 bases, 20 to 150 bases, 30 to 100 bases, and 50 to 80 bases. As one example, particularly, the single-stranded nucleic acid region 113B having a 5' end has a sequence composed of thymine as a base sequence up to at least the 2nd base, preferably up to the 5th base, more preferably up to the 7th base, each from the 5' end. The single-stranded nucleic acid region 113B having a 5' end may have a base sequence 90% or more, preferably 100% of which is thymine. When the single-stranded nucleic acid region 113B having a 5' end has a base sequence composed of thymine as a base sequence up to the 2nd base, preferably up to the 5th base, more preferably up to the 7th base, each from the terminal portion or when the percentage of thymine in the single-stranded nucleic acid region 113B having a 5' end is adjusted to fall within the aforesaid range, the formation of a higher structure can be prevented and the shape facilitating the introduction in the nanopore 101 can be maintained.

The term "block molecule 201" as used herein means a molecule having a function of preventing a bio-adapter molecule complex 202 present in the first liquid tank 104A and Unziped into a single strand from coming off into the second liquid tank 104B via the nanopore 101. Therefore, the block molecule 201 may be a molecule which is bound to the single-stranded nucleic acid region 113A or may have a higher structure formed in the vicinity of the end of the single-stranded nucleic acid region 113B. Examples of a molecule usable as the block molecule 201 include avidin, streptavidin, and a complex between an anti-DIG antibody, which is an antibody against Digoxigein (DIG), and a bead. Examples of the higher structure usable as the block molecule 201 include an intramolecular hairpin structure and a triple-stranded DNA structure, each famed at the 3' end portion of the single-stranded nucleic acid region 113A.

The block molecule 201 has preferably a size (diameter) larger than that of the nanopore 101. For example, as the size of the block molecule 201 relative to the diameter of the nanopore 101, it may be large enough to stop the advance of the biomolecule 109 and for example, it is preferably about 1.2 to 50 times larger than the biomolecule. More specifically, when a single-stranded DNA is measured as the biomolecule 109, it has a diameter of about 1.5 nm. Supposing that the nanopore 101 has a diameter of about 1.5 nm to 2.5 nm, streptavidin (diameter: about 5 nm) can therefore be used as the block molecule 201. When streptavidin is bound to the end of the single-stranded nucleic acid region 113A, biotin is bound to this end in advance. The end may be biotinylated by a commercially available kit. Although streptavidin is not particularly limited, it may be, for example, a mutant streptavidin obtained by introducing mutation in streptavidin to have one binding site to biotin.

On the other hand, the substrate 102 is made of a base material 120 and a thin film 121 formed on one of the main surfaces of the base material 120. The nanopore 101 is formed in the thin film 121. Although not illustrated, the substrate 203 may have an insulating layer. The base material 120 may be formed from a material of electrical insulators, for example, an inorganic material or organic material (including a polymer material). Examples of the material of electrical insulators constituting the base material 120 include silicon (silicon), silicon compounds, glass, quartz, polydimethylsiloxane (PDMS), polytetrafluoroethylene (PTFE), polystyrene, and polypropylene. Examples of the silicon compounds include silicon nitride, silicon oxide, silicon carbide, and silicon oxynitride. In particular, the base material 120 may be made of any of the aforesaid materials and the material may be, for example, silicon or the silicon compound.

The size and thickness of the substrate 102 is not particularly limited as far as they permit formation of the nanopore 101. The substrate 102 can be formed by a method known in the art or it may be available as a commercial product. For example, the substrate 102 can be formed using photolithography or electron beam lithography, or a technique such as etching, laser ablation, injection molding, casting, molecular beam epitaxy, chemical vapor deposition (CVD), dielectric breakdown, electron beam, or focused ion beam. The substrate 102 may be coated to avoid adsorption of a non-target molecule to the surface.

The substrate 102 has at least one nanopore 101. The nanopore 101 is formed in the thin film 121 but in some cases, it may be formed in the thin film 121 and the base material 120. The tam. "nanopore" or "pore" as used herein means a through-hole having a nanometer (nm) size (that is, having a diameter of 1 nm or more and less than 1 μm) and penetrates the substrate 102 to communicate the first liquid tank 104A with the second liquid tank 104B.

The substrate 102 preferably has the thin film 121 to provide the nanopore 101 therein. The nanopore 101 can be formed in the substrate 102 easily and efficiently by forming, on the substrate 120, the thin film 121 made of a material and having a thickness, each suited for the formation of a nanosize pore. In view of the easy formation of the nanopore 101, the material of the thin film 121 is preferably, for example, silicon oxide ($SiO_2$), silicon nitride (SiN), silicon oxynitride (SiON), a metal oxide, or a metal silicate. The thin film 121 (in some cases, the entire substrate 102) may be substantially transparent. The term "substantially transparent" as used herein means that the film transmits about 50% or more, preferably 80% or more of an external light. The thin film may be either a single layer or a plurality of layers.

The thin film 121 has a thickness of 1 nm to 200 nm, preferably 1 nm to 50 nm, more preferably 1 nm to 20 nm. The thin film 121 may be formed on the base material 120 by a method known in the art, for example, low-pressure chemical vapor deposition (LPCVD).

An insulating layer is preferably famed on the thin film 121. The thickness of the insulating layer is preferably 5 nm to 50 nm. Any insulator material may be used for the insulating layer and, for example, silicon or a silicon compound (such as silicon nitride or silicon oxide) is preferably used.

The appropriate size of the nanopore 101 may be selected depending on a biopolymer to be analyzed. The nanopore may have a uniform diameter or may have a diameter different from site to site. The nanopore formed in the thin film 121 of the substrate 102 has a minimum diameter portion, that is, the minimum diameter which the nanopore 101 has, of 100 nm or less, for example, 1 nm to 100 nm, preferably 1 nm to 50 nm, for example, 1 nm to 10 nm; more specifically, 1 nm or more and 5 nm or less, 3 nm or more to 5 nm or less, or the like. The nanopore 101 may be linked to a pore formed in the base material 120 and having a diameter of 1 μm or more.

When a biomolecule to be analyzed is a single-stranded nucleic acid (DNA), the single-stranded DNA has a diameter of about 1.5 nm, so that the diameter of the nanopore 101 is preferably about 1.5 nm to 10 nm, more preferably about 1.5 nm to 2.5 nm. When a biomolecule to be analyzed is a double-stranded nucleic acid (DNA), the double-stranded DNA has a diameter of about 2.6 nm, so that the diameter of the nanopore 101 is preferably about 3 nm to 10 nm, more preferably about 3 nm to 5 nm. The diameter of the nanopore 101 may be determined as needed, depending on the outer diameter of a biopolymer to be analyzed (for example, a protein, a polypeptide, or a sugar chain).

The depth (length) of the nanopore 101 can be adjusted by adjusting the thickness of the thin film 121 or the entire substrate 102. The depth of the nanopore 101 is preferably made equal to the length of a monomer unit constituting a biomolecule to be analyzed. For example, when a nucleic acid is selected as a biomolecule to be analyzed, the depth of the nanopore 101 is preferably made equal to or less than the size of one base, for example, 0.3 nm or less. The shape of the nanopore 101 is basically round, but it may be oval or polygonal.

Further, at least one nanopore 101 may be provided in the substrate 102. When a plurality of nanopores 101 is provided, they may be arranged regularly or randomly. The nanopore 101 may be famed by a method known in the art, for example, by irradiating an electron beam from a transmission electron microscope (TEM) and using nanolithography or ion beam lithography.

In the analysis apparatus shown in FIG. 1, a pair of liquid tanks 104A and 104B has one nanopore 101 therebetween, but this is only an example. The pair of liquid tanks 104A and 104B may have a plurality of nanopores 101 therebetween. Another example is an array device in which the substrate 102 has a plurality of nanopores 101 therein and respective regions having nanopores 101 are separated from one another by a partition. In this array device, the first liquid tank 104A may be a common tank and the second liquid tank 104B may be a plurality of individual tanks. In this case, electrodes may be placed in each of the common tank and the individual tanks.

The first electrode 105A and the second electrode 105B are not particularly limited and they may be formed using, for example, a platinum-group material such as platinum, palladium, rhodium, or nickel, a graphite such as graphene (composed of either a single layer or a plurality of layers), tungsten, tantalum, or the like.

Figure 3:
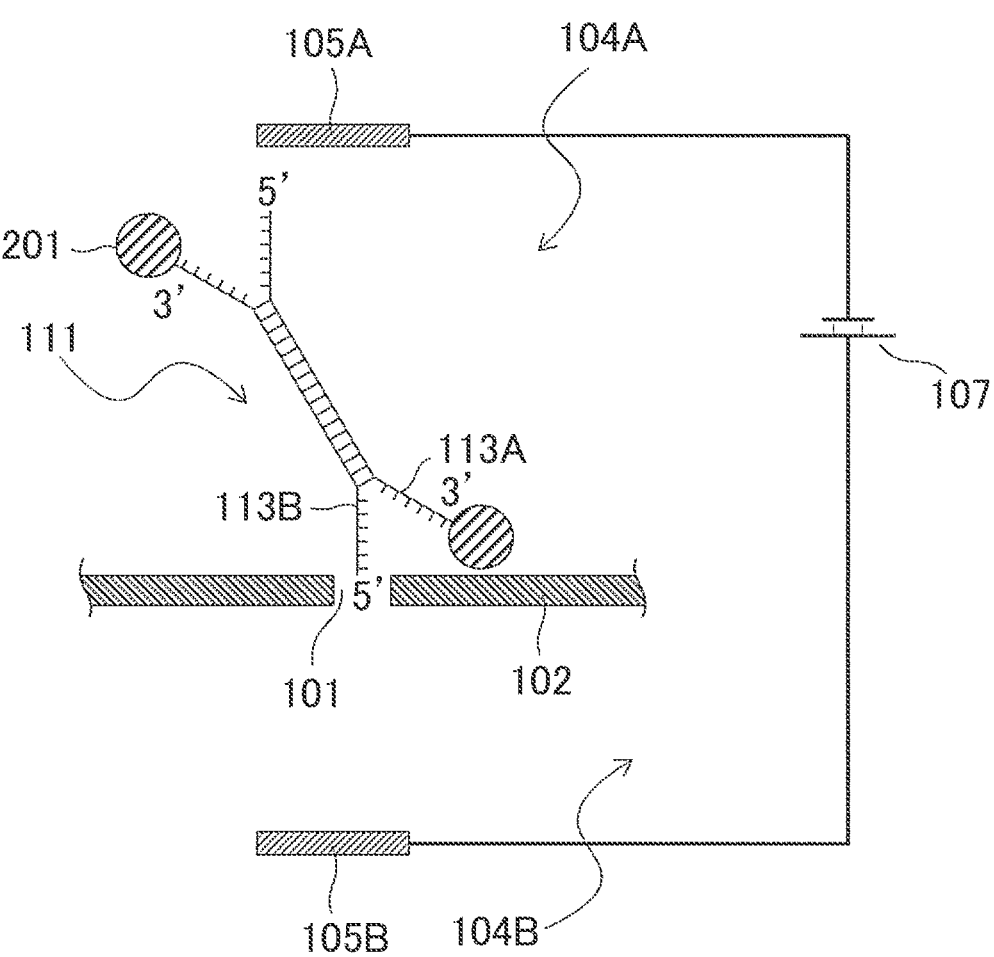
FIG. 3 is a block diagram schematically showing a step of analyzing a biomolecule by using the adapter molecule according to the first embodiment.
Figure 4:
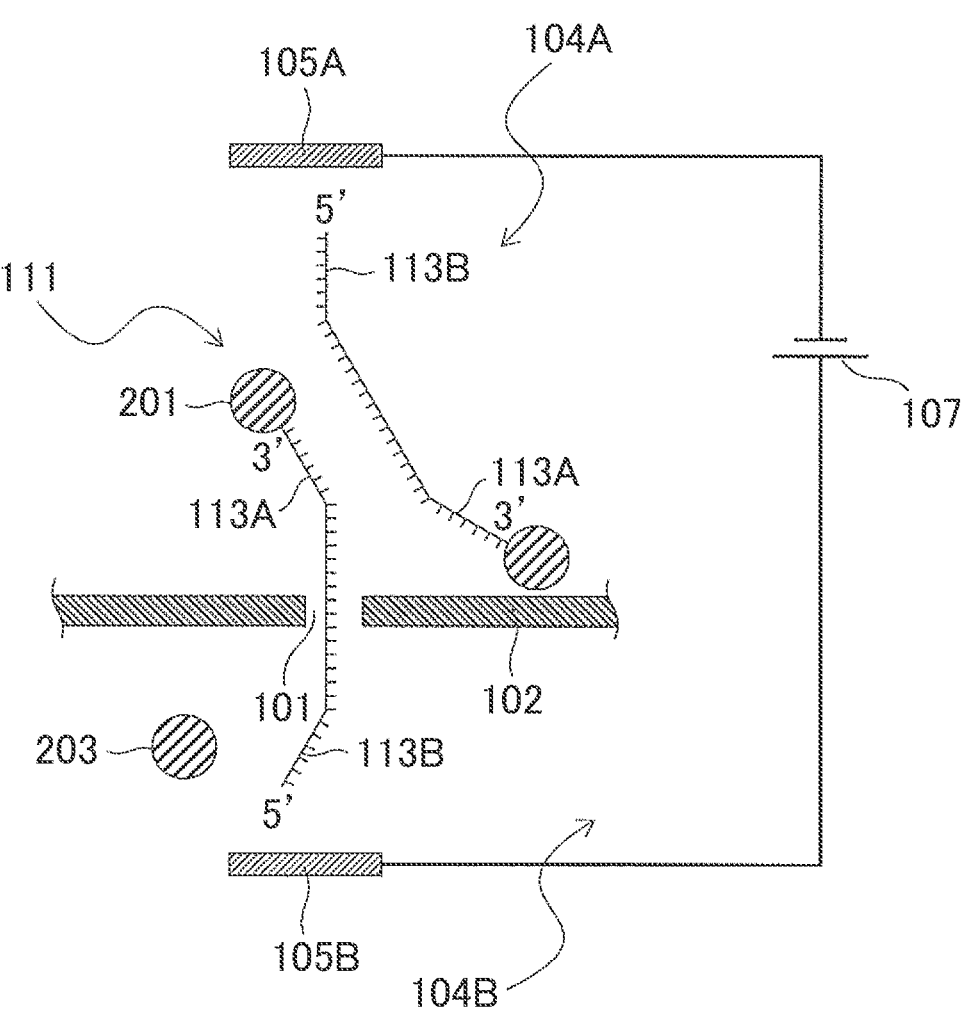
FIG. 4 is a block diagram schematically showing the step of analyzing a biomolecule by using the adapter molecule according to the first embodiment, which follows the step shown in FIG. 3.

In the biomolecule analysis apparatus having a structure as described above, by applying a voltage to between the first electrode 105A and the second electrode 105B while filling the first liquid tank 104A with the electrolyte solution 103 containing the bio-adapter molecule complex 111 and thereby forming a potential gradient with the first liquid tank 104A as a negative potential or a ground potential and the second liquid tank 104B as a positive potential, the single-stranded nucleic acid region 113B not having the block molecule 201 passes via (through) the nanopore 101 and transfers in the direction of the second liquid tank 104B as shown in FIG. 3. Then, as shown in FIG. 4, by the potential gradient between the first liquid tank 104A and the second liquid tank 104B, the bio-adapter molecule complex 111 passes via (through) the nanopore 101 and transfers to the second liquid tank 104B. During the change in state from FIG. 3 to FIG. 4, a double-stranded nucleic acid (the double-stranded nucleic acid region 112 in the adapter molecule 110 and the biomolecule 109) in the bio-adapter molecule complex 111 is detached (Unziped).

It is to be noted that a voltage gradient may be formed between the first liquid tank 104A and the second liquid tank 104B so that either one of the two tanks has a positive potential and the other tank has a negative potential or a ground potential in order to transfer a negatively charged nucleic acid molecule. When one of the first liquid tank 104A and the second liquid tank 104B has a positive potential and the other tank has a negative potential in the following description, it is needless to say that the liquid tank with the negative potential may have a ground potential.

Figure 5:
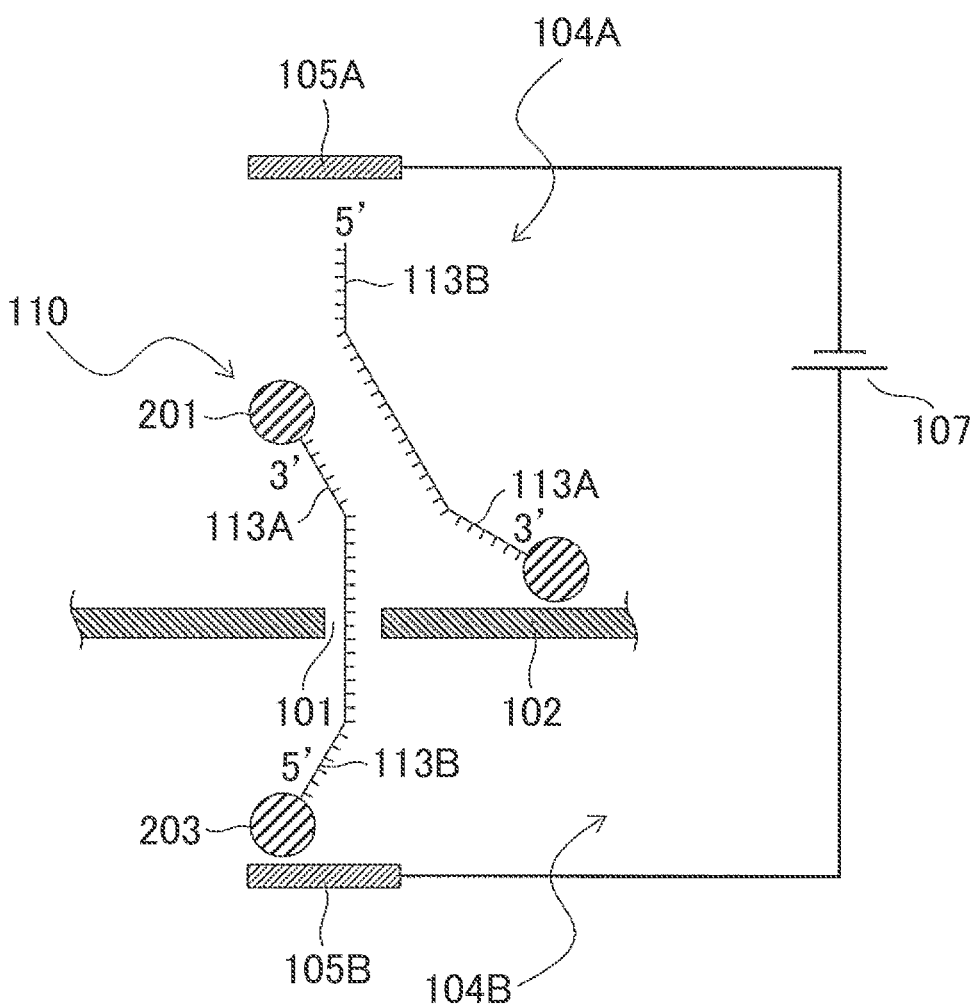
FIG. 5 is a block diagram schematically showing the step of analyzing a biomolecule by using the adapter molecule according to the first embodiment, which follows the step shown in FIG. 4.

As shown in FIGS. 3 and 4, by filling the second liquid tank 104 with the electrolyte solution 103 having the block molecule 203 while the single-stranded nucleic acid region 113B not having the block molecule 201 passes through the nanopore 101 and transfers in the direction of the second liquid tank 104B, the block molecule 203 binds to the end of the single-stranded nucleic acid region 113B as shown in FIG. 5. This makes it possible to place the block molecules 201 and 203 at each end of the bio-adapter molecule complex 111 converted into a single strand.

In the present embodiment, the block molecules 201 and 203 may be the same substance or different substances. The block molecule 201 may be famed as a higher structure in the vicinity of the terminal portion of the single-stranded nucleic acid region 113A and the block molecule 203 may be a substance which binds to the terminal portion of the single-stranded nucleic acid region 113A.

As an example of using respectively different substances as the block molecules 201 and 203, the block molecule 201 which binds to the terminal portion of the single-stranded nucleic acid region 113A may be streptavidin and the block molecule 203 which binds to the terminal portion of the single-stranded nucleic acid region 113B is a bead bound via a DIG-anti-DIG antibody binding. In this case, the single-stranded nucleic acid region 113B is labeled with Digox-igein (DIG) in advance. As shown in FIG. 4, the single-stranded nucleic acid region 113B having an end labeled with DIG is migrated from the first liquid tank 104A to the second liquid tank 104B. Since the DIG itself is sufficiently smaller than the diameter 1 nm of the nanopore 101, the end of the single-stranded nucleic acid region 113B is introduced in the nanopore 101 first. A bead having a diameter larger than 1 nm and labeled with an anti-DIG antibody is introduced in the second liquid tank 104B to bind it to the DIG which has labeled the end of the single-stranded nucleic acid region 113B, while the bio-adapter molecule complex 202 converted into a single strand being stopped from moving by the block molecule 201 composed of streptavidin. This makes it possible to bind the block molecule 201 composed of streptavidin and the block molecule 203 composed of the bead obtained via the DIG-anti-DIG antibody binding to the bio-adapter molecule complex 111 converted into a single strand. Instead of using the biotin-streptavidin and the DIG-anti-DIG bound bead, the block molecules 201 and 203 may be bound to the complex by a method of thiolating the end and binding gold particles thereto or by a method of modifying the end with an amino group and binding it to a carboxyl-modified bead by a dehydration reaction. The block molecules 201 and 203 may be those obtained by hybridizing a near-field region including the end with an oligonucleotide having a sequence complementary thereto and then firmly binding the resulting double-stranded nucleic acid region to the complex by photocrosslinking or by using a crosslinking agent such as ethidium bromide amide monoazide or a psoralen derivative.

The aforesaid example describes a method of binding the block molecule 201 to the terminal portion of the single-stranded nucleic acid region 113A and then binding the block molecule 203 to the terminal portion of the single-stranded nucleic acid region 113B. This binding order may be reversed as follows: the block molecule 203 may be bound to the terminal portion of the single-stranded nucleic acid region 113B and then, the block molecule 201 may be bound to the terminal portion of the single-stranded nucleic acid region 113A.

During the change in state from FIG. 3 to FIG. 4, using the adapter molecule 110 makes it possible to convert the biomolecule 109 which is a double-stranded nucleic acid into a single-stranded nucleic acid capable of passing through the nanopore 101, without subjecting the biomol-ecule to a cumbersome modification treatment (for example, heat treatment). In short, the double-stranded nucleic acid can easily be detached using the adapter molecule 110.

Figure 6A:
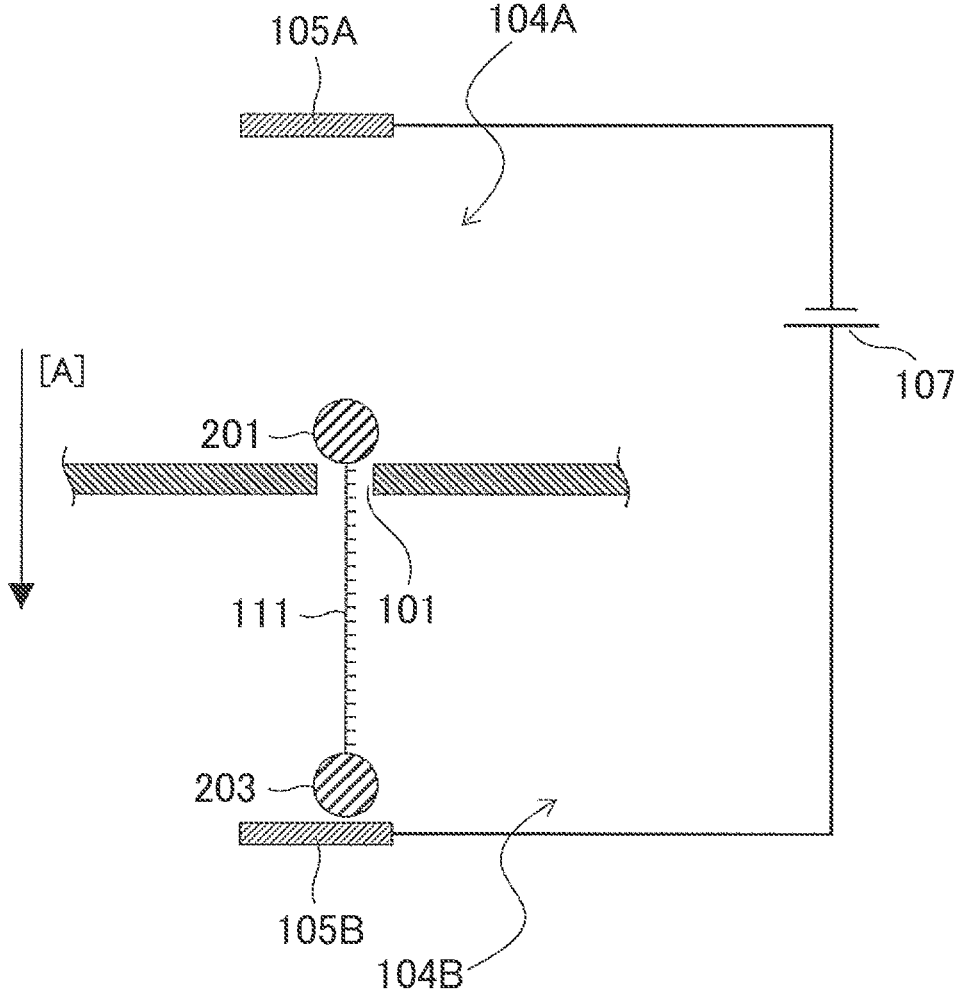
FIG. 6A is a block diagram schematically showing the step of analyzing a biomolecule by using the adapter molecule according to the first embodiment, which follows the step shown in FIG. 5.
Figure 6B:
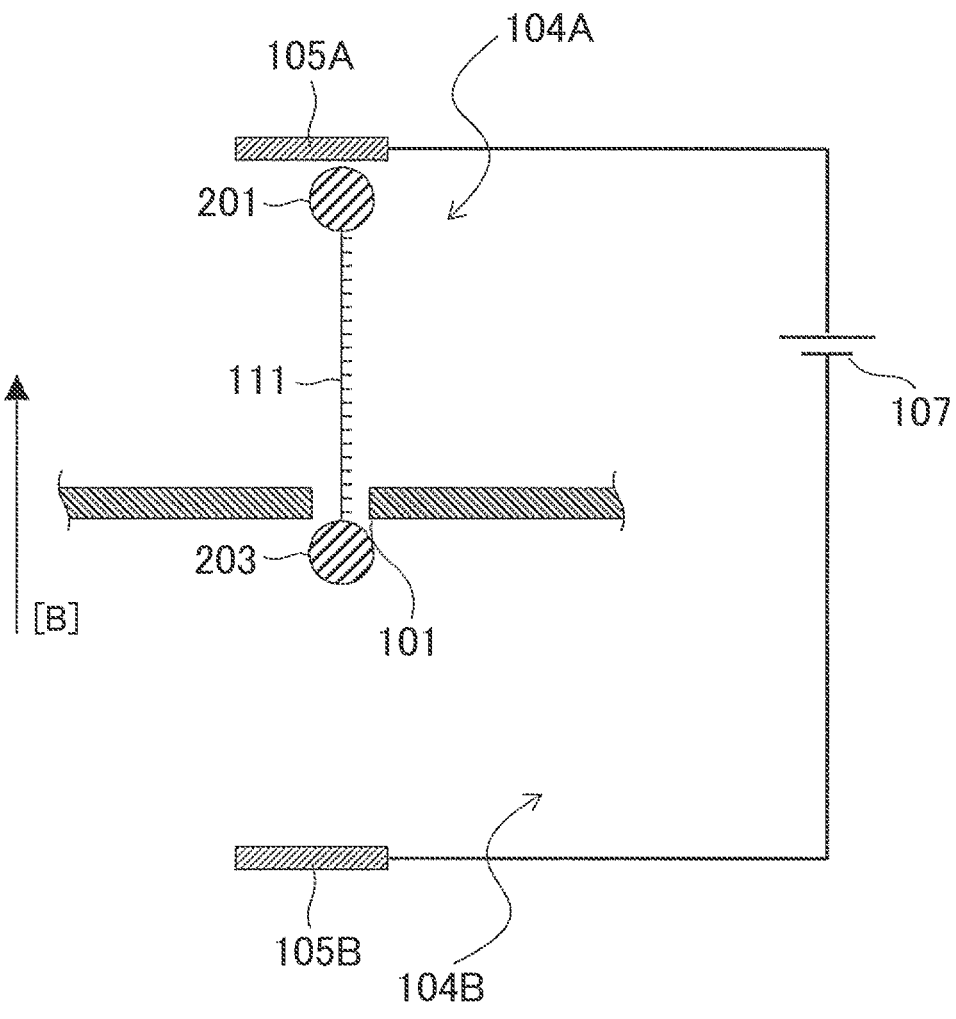
FIG. 6B is a block diagram schematically showing the step of analyzing a biomolecule by using the adapter molecule according to the first embodiment, which follows the step shown in FIG. 5.

The biomolecule analysis apparatus transfers the bio-adapter molecule complex 111 converted into a single strand from the first liquid tank 104A to the second liquid tank 104B via the nanopore 101 as shown in FIG. 4, but can transfer the bio-adapter molecule complex 111 converted into a single strand from the second liquid tank 104B to the first liquid tank 104A via the nanopore 101 by reversing the voltage gradient. Described specifically, as shown in FIG. 6A, the bio-adapter molecule complex 111 converted into a single strand can be transferred in the direction of the arrow [A] in the drawing by a voltage gradient formed with the first liquid tank 104A as a negative potential and the second liquid tank 104B as a positive potential. On the contrary, as shown in FIG. 6B, the bio-adapter molecule complex 111 converted into a single strand can be transferred in the direction of the arrow [B] in the drawing by a voltage gradient formed with the second liquid tank 104B as a negative potential and the first liquid tank 104A as a positive potential. Thus, the biomolecule analysis apparatus can reciprocate the bio-adapter molecule complex 111 converted into a single strand between the first liquid tank 104A and the second liquid tank 104B.

In the biomolecule analysis apparatus shown in FIG. 1, a measurement section 106 measures an ionic current (block current) flowing between a pair of electrodes 105A and 105B and a computer 108 gets data on the sequence of the bio-adapter molecule complex 111 based on the value of the ionic current (block current) thus measured. Although not shown in FIG. 1, it is also possible to provide an electrode in the nanopore 101 to obtain a tunnel current to get data on the sequence based on the tunnel current or to detect a change in the characteristic of a transistor and thereby get data on the sequence of the biomolecule 109.

Here, a method of determining the data on the base sequence will be described more specifically. There are four bases, that is, ATGC and when these bases pass through the nanopore 101, ionic current (block current) values specific to them are observed respectively. Therefore, an ionic cur-rent of a known sequence at the time when it passes through the nanopore 101 is measured in advance and a current value corresponding to the known sequence is stored in the memory of the computer 108. By comparing the current values measured at the time when the bases constituting the bio-adapter molecule complex 111 to be analyzed pass through the nanopore 101 successively with the current values corresponding to the known sequence stored in the memory, the kinds of the bases constituting the bio-adapter molecule complex 111 to be analyzed can be determined successively.

The base sequence of the biomolecule 109 may also be determined by labeling the biomolecule 109 with a phos-phor, exciting it in the vicinity of the nanopore 101, and detecting the fluorescence thus emitted. It is also possible to use a hybridization-based method of determining the base sequence of the biomolecule 109 as described in Reference Literature 1 (NANO LETTERS (2005), Vol. 5, pp. 421-424).

By the aforesaid method of determining the base sequence data, the base sequence data of the biomolecule 109 can be obtained when the bio-adapter molecule complex 111 con-verted into a single strand is transferred from the first liquid tank 104A to the second liquid tank 104B via the nanopore 101 as shown in FIGS. 3 and 4. The base sequence data of the biomolecule 109 can also be obtained when the bio-adapter molecule complex 111 converted into a single strand is reciprocated between the first liquid tank 104A and the second liquid tank 104B via the nanopore 101 as shown in FIGS. 6A and 6B. FIGS. 6A and 6B schematically show that at this time, the block molecules 201 and 203 can prevent the entire bio-adapter molecule complex 111 converted into a single strand from passing through the nanopore 101.

When the bio-adapter molecule complex 111 converted into a single strand is reciprocated, the base sequence data of the biomolecule 109 may be obtained only during the transfer in the direction of the arrow [A] in FIG. 6A; the base sequence data of the biomolecule 109 may be obtained only during the transfer in the direction of the arrow [B] in FIG. 6B; or the base sequence data of the biomolecule 109 may be obtained in each of the directions of the arrow [A] in FIG. 6A and the arrow [B] in FIG. 6B. During the transfer in the direction of the arrow [A] in FIG. 6A, the base sequence data are determined from the 5' end to the 3' end of the biomolecule 109, while during the transfer in the direction of the arrow [B] in FIG. 6B, the base sequence data are determined from the 3' end to the 5' end of the biomolecule 109. In either case, a plurality of sets of the base sequence data of the biomolecule 109 can be obtained, so that the accuracy of the base sequence data is improved. In other words, by reciprocating the bio-adapter molecule complex 111 converted into a single strand, the base sequence of the biomolecule 109 can be read a plurality of times, leading to an improvement in the accuracy of reading.

The switching of an applied voltage in the aforesaid reciprocating movement is conducted, for example, by a method of automatically switching the voltage at regular intervals. In this case, the voltage switching timing is programmed into the computer 108 in advance and by controlling a voltage source 107 according to this program, the applied voltage may be switched at the aforesaid timing to conduct the reciprocating movement as described above.

Alternatively, the applied voltage can be switched based on the base sequence data obtained during the aforesaid reciprocating movement. For example, a characteristic sequence or a region different from a base (AGCT) and causing a block current is incorporated in the adapter molecule 110 in advance and a voltage is switched when the signal of this characteristic sequence or the region is read. Examples of the region different from the base and causing a block current include regions containing a pseudo nucleic acid such as peptide nucleic acid, artificial nucleic acid, or the like. By reading the signal of the characteristic sequence or the region different from the base and causing a block current, it is possible to find that the reading of the base sequence of the biomolecule 109 is completed and the terminal portion of the bio-adapter molecule complex 111 comes close to the nanopore 101. The applied voltage is switched at this timing to transfer the bio-adapter molecule complex 111 in an opposite direction before the bio-adapter molecule complex 111 falls off from the nanopore 101. Further, in the present embodiment, the applied voltage in the aforesaid reciprocating movement may be switched by detecting the block molecules 201 and 203. More specifically, a decrease in the block current is measured when the block molecule 201 or 203 comes close to the nanopore 101, so that an applied voltage is switched when a decrease in the block current is detected.

Thus, a modification treatment of a double-stranded nucleic acid into a single-stranded nucleic acid becomes unnecessary by using the adapter molecule 110. This means that even when the biomolecule 109 to be analyzed is a double-stranded nucleic acid, it may be converted, by a voltage gradient formed between the first liquid tank 104A and the second liquid tank 104B, into a single-stranded nucleic acid whose base sequence can be determined. Then, sequence determining analysis may be performed in the aforesaid conventional method.

In the aforesaid example, a double-stranded nucleic acid (DNA or RNA) is mentioned as the biomolecule 109, but according to a principle similar to that described above, even a protein (peptide chain) or sugar chain may be analyzed as the biomolecule 109.

Second Embodiment

In the present embodiment, an adapter molecule 300 having a structure different from that of the adapter molecule 110 shown in FIG. 1 and the like will be described. In the adapter molecule 300 shown as an example in FIG. 7, a component same as that of the adapter molecule 110 shown in FIG. 1 or the like is identified by the same reference numeral and a detailed description on it will be omitted in this embodiment.

Figure 7:
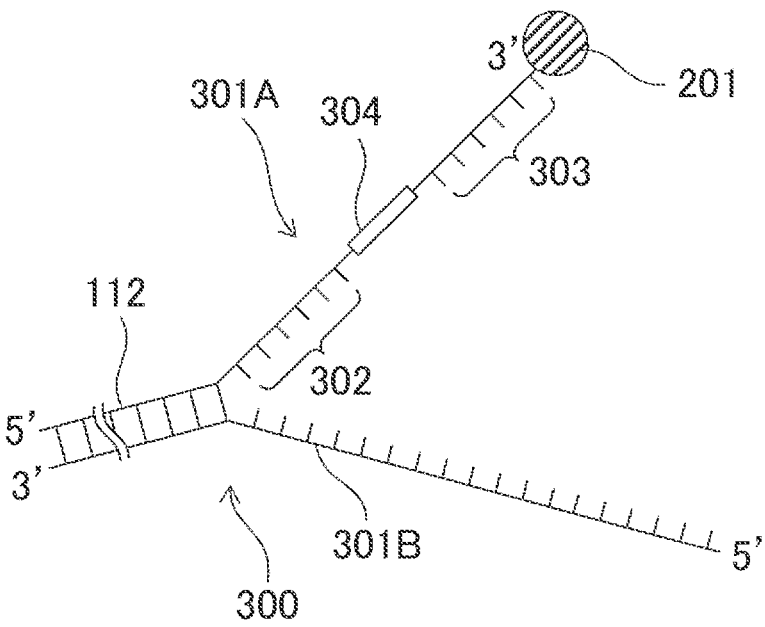
FIG. 7 is a block diagram schematically showing an adapter molecule according to a second embodiment.

The adapter molecule 300 shown in FIG. 7 has a double-stranded nucleic acid region 112 which binds to the biomolecule 109, a pair of single-stranded nucleic acid regions 301A and 301B which is linked to a terminal portion of the double-stranded nucleic acid region 112 different from a terminal portion which binds to the biomolecule 109 and is composed of base sequences non-complementary to each other, and a block molecule 201 placed at an end of either one of the single-stranded nucleic acid regions 301A and 301B. The single-stranded nucleic acid region 301A has a 3' end and the single-stranded nucleic acid region 301B has a 5' end. In the example shown in FIG. 7, the block molecule 201 is placed at the terminal portion of the single-stranded nucleic acid region 301A having a 3' end. The block molecule 201 may be placed not at the end of the single-stranded nucleic acid region 113A but at the terminal portion of the single-stranded nucleic acid region 301B having a 5' end.

The single-stranded nucleic acid region 301A of the adapter molecule 300 shown in FIG. 7 has a molecular motor binding site 302 to which a molecular motor can be bound. The term "molecular motor" as used herein means a protein molecule capable of moving on the adapter molecule 300 and the biomolecule 109. The molecular motor having such a function is not particularly limited and examples include DNA polymerase, RNA polymerase, ribosome, and helicase. In particular, in the present embodiment, DNA polymerase which synthesizes a complementary strand in the direction from a 5' end to a 3' end, with a single-stranded DNA as a template is preferably used as the molecular motor. The molecular motor binding site 302 is not limited to have a specific base sequence but may have any base sequence and it is present as a single-stranded nucleic acid.

The single-stranded nucleic acid region 301A in the adapter molecule 300 shown in FIG. 7 has, on the side of the 3' end of the molecular motor binding site 302, a primer binding site 303 with which a primer can be hybridized. The primer binding site 303 may have a sequence complementary to the base sequence of the primer to be used and the sequence is not specifically limited. The term "primer" as used herein is not particularly limited and it may be a single-stranded nucleotide having, for example, a length of 10 to 40 bases, preferably a length of 15 to 35 bases, more preferably a length of 18 to 25 bases. The primer binding site 303 is therefore a region which has a length of 10 to 40 bases, preferably a length of 15 to 35 bases, more preferably a length of 18 to 25 bases and is composed of a base sequence complementary to the base sequence of the primer.

The single-stranded nucleic acid region 301A in the adapter molecule 300 shown in FIG. 7 further has a spacer 304 between the molecular motor binding site 302 and the primer binding site 303. The term "spacer 304" as used herein means a region to which a molecular motor cannot bind, that is, a region not containing a base composed of AGCT. The spacer 304 is not particularly limited and it may be a linear linked body not containing a base. In particular, the length of the spacer 304 preferably corresponds to at least two bases, that is, about 0.6×2 nm or more. In other words, the spacer 304 can separate between the molecular motor binding site 302 and the primer binding site 303 from each other by two bases or more (about 0.6×2 nm or more). Examples of the material constituting the spacer 304 include materials which can be placed in a DNA chain, such as C3 Spcer, PC spacer, Spacer 9, Spacer 18, and dSpacer, each product of Integrated DNA Technologies, Inc. Additional examples of the material of the spacer 304 include linear carbon chains, linear amino acids, linear fatty acids, and linear sugar chains.

Further, the adapter molecule 300 shown in FIG. 7 has a predetermined region of the double-stranded nucleic acid region 112 as a labeling sequence (not shown). The labeling sequence is also called "barcode sequence" or "index sequence" and means a base sequence specific to the adapter molecule 300. For example, by using a plurality of adapter molecules 300 different only in labeling sequence which is prepared in advance, the kind of the adapter molecule 300 used can be identified based on the labeling sequence.

Figure 8A:
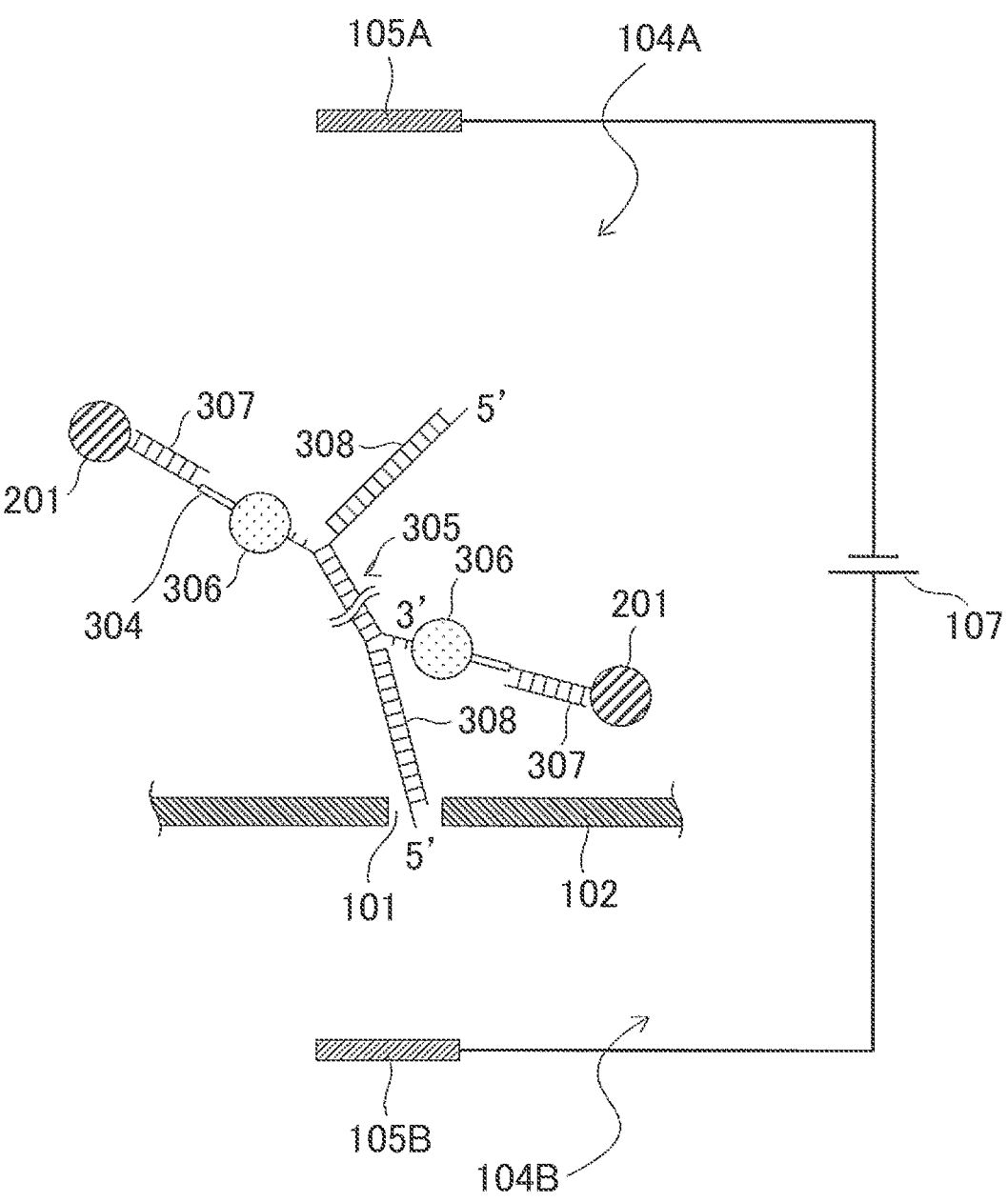
FIG. 8A is a block diagram schematically showing a step of analyzing a biomolecule by using the adapter molecule according to the second embodiment.

A method of analyzing the biomolecule 109 by using the adapter molecule 300 composed as described above will hereinafter be described with reference to FIGS. 8A and B and FIGS. 9A to G.

First, a bio-adapter molecule complex 305 having an adapter molecule 300 bound to both end portions of a biomolecule 109 is prepared. A first liquid tank 104A is filled with an electrolyte solution containing the resulting bio-adapter molecule complex 305, a molecular motor 306, a primer 307, and a blocking nucleic acid 308. Then, as shown in FIG. 8A, the molecular motor 306 is bound to a molecular motor binding site 302 of the adapter molecule 300, the primer 307 is hybridized with a primer binding site 303, and the blocking nucleic acid 308 is hybridized with a predetermined position of a single-stranded nucleic acid region 103B. The blocking nucleic acid 308 is a single-stranded nucleotide composed of a sequence complementary to the predetermined region of the single-stranded nucleic acid region 103B. The region with which the blocking nucleic acid 308 is hybridized is a region of the single-stranded nucleic acid region 103B other than the 5' end region (for example, 2 to 10 bases, preferably 5 to 10 bases including the 5' end). The blocking nucleic acid 308 is hybridized with the aforesaid region to prevent the molecular motor 306 from binding to the single-stranded nucleic acid region 301B, which improves a binding efficiency of the molecular motor 306 to the molecular motor binding site 302. In other words, even a small amount of the molecular motor 306 can be bound to the molecular motor binding site 302 efficiently. Even if the molecular motor 306 binds to the single-stranded nucleic acid region 301B, it does not affect the analysis results of the biomolecule 109. Use of the blocking nucleic acid 308 is therefore not required.

Figure 8B:
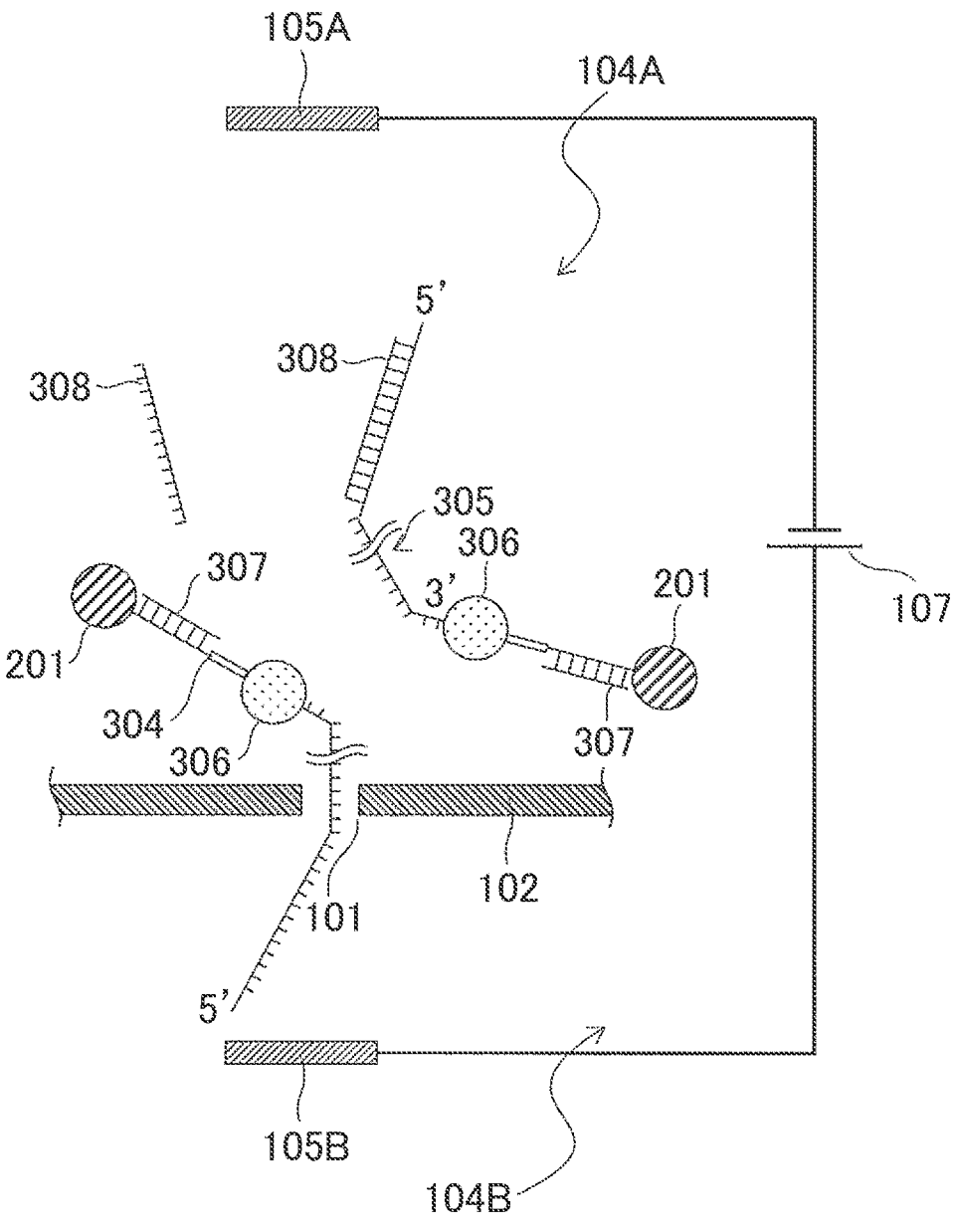
FIG. 8B is a block diagram schematically showing the step of analyzing a biomolecule by using the adapter molecule according to the second embodiment, which follows the step shown in FIG. 8A.

Next, a voltage is applied to between the first electrode 105A and the second electrode 105B to form a potential gradient with the first liquid tank 104A as a negative potential (or a ground potential. This will equally apply hereinafter) and with the second liquid tank 104B as a positive potential. By this potential gradient, the single-stranded nucleic acid region 113B transfers in the direction of the nanopore 101 and the 5' end region with which the blocking nucleic acid 308 is not hybridized is introduced in the nanopore 101. As shown in FIG. 8B, by the potential gradient between the first liquid tank 104A and the second liquid tank 104B, the bio-adapter molecule complex 305 passes via (through) the nanopore 101 and transfers to the second liquid tank 104B. At this time, the double-stranded nucleic acid of the bio-adapter molecule complex 305 (the double-stranded nucleic acid region 112 in the adapter molecule 300 and the biomolecule 109, and the blocking nucleic acid 308 and the single-stranded nucleic acid region 301B) is detached (Unziped).

Even if the adapter molecule 300 is used in such a manner, the biomolecule 109 which is a double-stranded nucleic acid can be converted into a single-stranded nucleic acid capable of passing through the nanopore 101 without a cumbersome modification treatment (for example, heat treatment). In short, even if the adapter molecule 300 is used, a double-stranded nucleic acid can easily be detached. In FIGS. 8A and B, the primer 307 and the molecular motor 306 are separated from each other by a length corresponding to the spacer 304, so that a complementary strand synthesis reaction by the molecular motor 306 with the 3' end of the primer 307 as a starting point does not occur. Although not shown in the drawing, as in First Embodiment, the block molecule 201 can be bound to the single-stranded nucleic acid region 103B of the bio-adapter molecule complex 305 in the second liquid tank 104B.

Figure 9A:
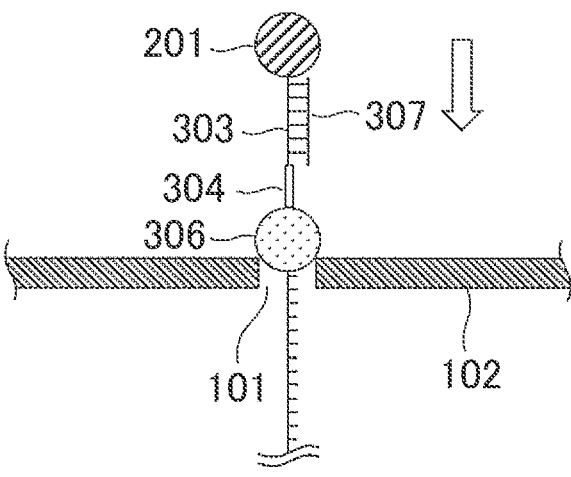
FIG. 9A is a block diagram schematically showing the main part in the step of analyzing a biomolecule by using the adapter molecule according to the second embodiment.
Figure 9B:
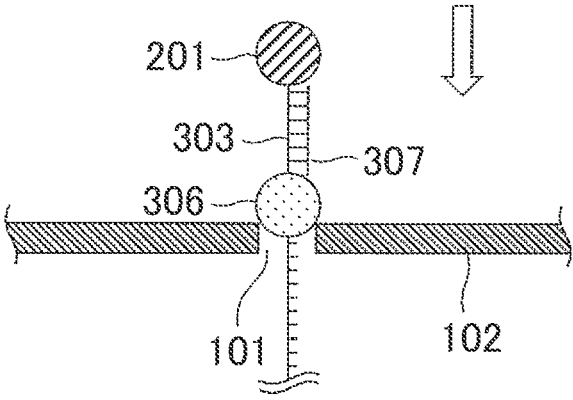
FIG. 9B is a block diagram schematically showing the main part in the step of analyzing a biomolecule by using the adapter molecule according to the second embodiment, which follows the step shown in FIG. 9A.

As shown in FIG. 9A, by the potential gradient between the first liquid tank 104A and the second liquid tank 104B, the bio-adapter molecule complex 305 converted into a single strand passes through the nanopore 101 and then, the molecular motor 306 reaches the nanopore 101. The dimension Dm of the molecular motor 306 is larger than the diameter Dn of the nanopore 101 (Dm>Dn), so that when the molecular motor 306 reaches the inlet of the nanopore 101 (on the side of the first liquid tank 104A), it is prevented from passing through the nanopore 101 and advancing to the outlet side (the side of the second liquid tank 104B) and stays at the inlet of the nanopore 101. On the other hand, the bio-adapter molecule complex 305 converted into a single strand is negatively charged, so that it advances in the downstream direction and causes a morphological change around the spacer 304. Then, the molecular motor 306 is brought into contact with the 3' end of the primer 307 and binds thereto (FIG. 9B). Then, the molecular motor 306 initiates a complementary strand synthesis reaction in the direction from the 5' end to the 3' end, with the 3' end of the primer 307 as a starting point. It is to be noted that a blank arrow in FIGS. 9A to H means a potential gradient from a negative electrode to a positive electrode.

Figure 9C:
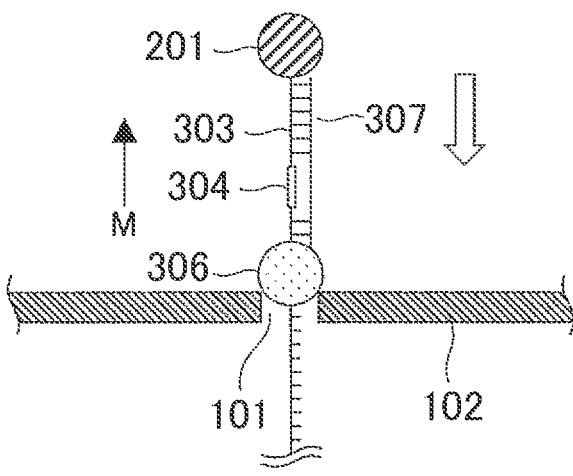
FIG. 9C is a block diagram schematically showing the main part in the step of analyzing a biomolecule by using the adapter molecule according to the second embodiment, which follows the step shown in FIG. 9B.

Then, as shown in FIG. 9C, when the complementary strand synthesis reaction by the molecular motor 306 proceeds, the bio-adapter molecule complex 305 converted into a single strand is transferred in the direction of the first liquid tank 104A (in the direction of the arrow M in FIG. 9C) against the potential gradient because the force of the molecular motor 306 to pull up the bio-adapter molecule complex 305 converted into a single strand is stronger than the potential gradient-derived force to move the bio-adapter molecule complex 305 converted into a single strand to the side of the second liquid tank 104B. At this time, the base sequence data of the bio-adapter molecule complex 305 passing through the nanopore 101 can be obtained.

Figure 9D:
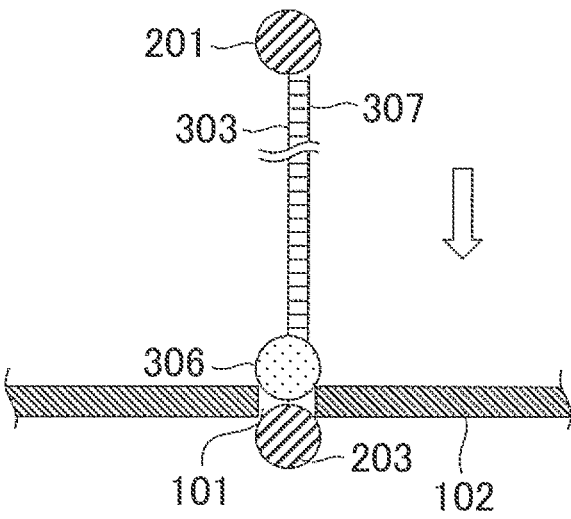
FIG. 9D is a block diagram schematically showing the main part in the step of analyzing a biomolecule by using the adapter molecule according to the second embodiment, which follows the step shown in FIG. 9C.
Figure 9E:
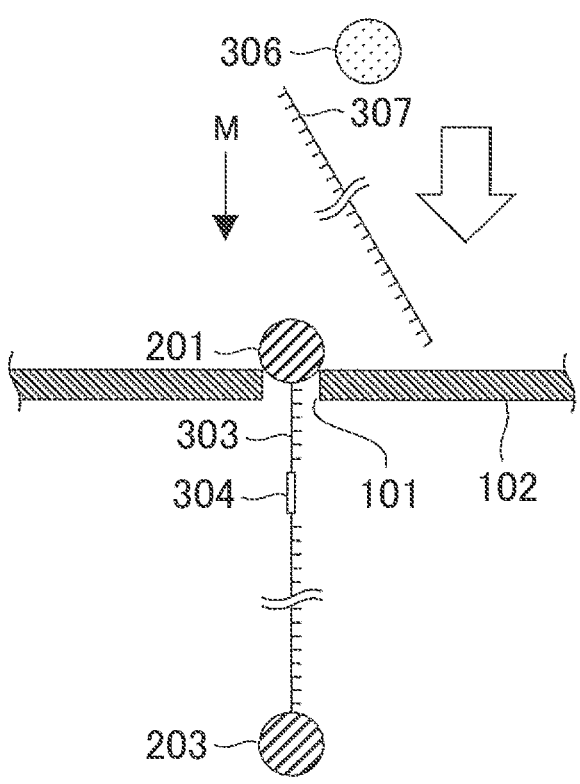
FIG. 9E is a block diagram schematically showing the main part in the step of analyzing a biomolecule by using the adapter molecule according to the second embodiment, which follows the step shown in FIG. 9D.

As shown in FIG. 9D, when the block molecule 203 bound to the single-stranded nucleic acid region 103B of the bio-adapter molecule complex 305 reaches the nanopore 101, the transfer motion by the molecular motor 306 and sequencing stop. At the stage when the transfer motion by the molecular motor 306 and sequencing stop, the positive potential in the second liquid tank 104B is made stronger. As a result, as shown in FIG. 9E, the bio-adapter molecule complex 305 transfers to the side of the second liquid tank 104B by the potential gradient (in the direction of the arrow M in FIG. 9E). At this time, a complementary strand 307 of the bio-adapter molecule complex 305 synthesized by the molecular motor 306 is detached (unziped) from the bio-adapter molecule complex 305 and at the same time, the molecular motor 306 departs from the bio-adapter molecule complex 305.

The timing of making the positive potential in the second liquid tank 104B stronger is determined by a method of automatically switching at regular intervals or a method of switching based on the base sequence data obtained. Since a decrease in block current can be measured when the block molecule 203 comes close to the nanopore 101, the positive potential in the second liquid tank 104B may be made stronger at the stage when a decrease in block current is detected. In any of these methods, the block molecule 203 can be bound to the single-stranded nucleic acid region 103B to prevent the entire bio-adapter molecule complex 305 converted into a single strand from passing through the nanopore 101.

Figure 9F:
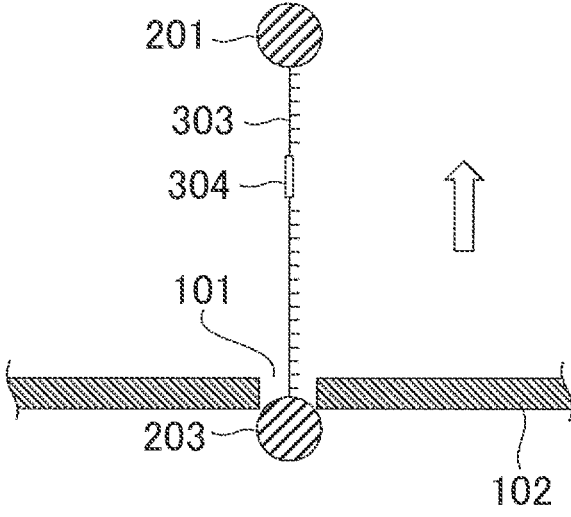
FIG. 9F is a block diagram schematically showing the main part in the step of analyzing a biomolecule by using the adapter molecule according to the second embodiment, which follows the step shown in FIG. 9E.

The, as shown in FIG. 9F, voltages to be applied to the first electrode 105A and the second electrode 105B are reversed to form a potential gradient with the first liquid tank 104A as a positive potential and the second liquid tank 104B as a negative potential. This makes it possible to transfer the bio-adapter molecule complex 305 converted into a single strand in the direction from the second liquid tank 104B to the first liquid tank 104A via the nanopore 101.

Figure 9G:
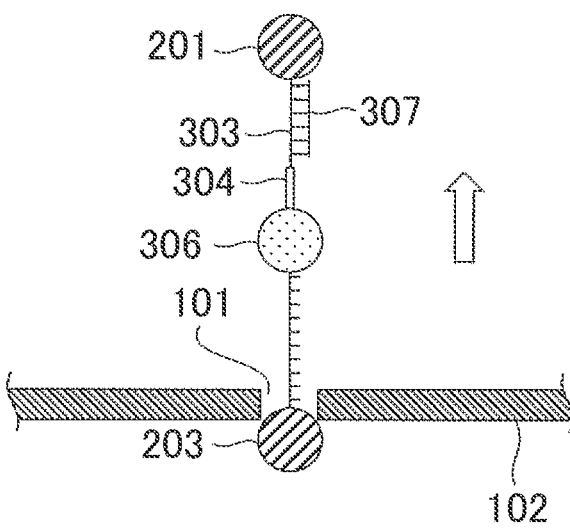
FIG. 9G is a block diagram schematically showing the main part in the step of analyzing a biomolecule by using the adapter molecule according to the second embodiment, which follows the step shown in FIG. 9F.

Then, as shown in FIG. 9G, the molecular motor 306 and the primer 307 are added to the electrolyte solution 103 poured in the first liquid tank 104A to hybridize the primer 307 with the primer binding site 303 and bind the molecular motor 306 to the molecular motor binding site 302. Then, voltages applied to the first electrode 105A and the second electrode 105B are reversed again to form a potential gradient with the first liquid tank 104A as a negative potential and the second liquid tank 104B as a positive potential. By this potential gradient, the bio-adapter molecule complex 305 with which the primer 307 is hybridized and to which the molecular motor 306 is bound is transferred in the direction of the second liquid tank 104B. And, as shown in FIG. 9B, a morphological change with the spacer 304 as a center occurs and the molecular motor 306 is brought into contact with the 3' end of the primer 307. In short, by repeating the operations shown in FIGS. 9A to G sequencing can be performed at every transfer motion by the molecular motor 306.

Reference Literature (Nat Nanotechnol. 2010. November; 5(11): 798-806) suggests that measurement using the molecular motor 306 (diameter of the nanopore 101: 1.4 nm) is performed while applying a voltage of at least 80 mV or more. In this case, according to Reference Literature (Nature physics, 5, 347-351, 2009), a force of about 24 pN is applied. In the present embodiment, therefore, in the measurement at a voltage of 80 mV, the block molecules 201 and 203 are preferably bound to the single-stranded nucleic acid regions 103A and 103B at a binding force of 24 pN or more.

EXAMPLE

The present invention will hereinafter be described more specifically by Example, but the technical scope of the present invention is not limited by the following Example.

Example 1

Reagents used in the present Example are shown in Table 1. In the present Example, an adapter molecule 300 having an abasic sequence portion (iSpC3) as the spacer 304 was prepared. In the present Example, as the molecular motor 306, BST 3.0 polymerase, a highly salt-tolerant DNA polymerase was used. Further, as a substrate for a BST 3.0 polymerase reaction, special bases (AMP, GMP, and UMP-PNP) and dTTP which were confirmed to clarify a single base unit signal were used.

TABLE 1

| Reagent | Product code | Maker |
| --- | --- | --- |
| CaCl$_2$ | 038-19735 | Wako Pure Chemical Industries |
| KCl | 160-22115 | Wako Pure Chemical Industries |
| MgCl$_2$ | 136 · 03995 | Waka Pure Chemical Industries |
| H$_2$SO$_4$ | N.A. | Kanto Chemical Co. |
| H$_2$O$_2$ | N.A. | Kanto Chemical Co. |
| KOH | 32344-00 | Kanto Chemical Co. |
| 1M Tris-HCl Buffer (pH 7.5) | 15567-027 | Invitrogen |
| BST 3.0 DNA polymerase | M0374M | New England B10labs |
| 10× Isothermal Buffer II | B0374S | New England B10labs |
| dNTP Mix (dATP, dGTP, dTTP, dCTP) | N0447L | New England B10labs |
| AMP-PNP | A2647-5MG | Sigma-Aldrich |
| GMP-PNP | G0635-5MG | Sigma-Aldrich |
| UMP-PNP | NU-4158 | Jena Bioscience |
| Blunt/TA Ligase Master Mix | M0367S | New England Biolabs |
| NEBNext ® Ultra ™ II End Repair/dA-Tailing Module | E7546L | New England B10labs |

In the present Example, a sequencer library for analyzing the base sequence of a double-stranded DNA (the biomolecule 109) was prepared according to the scheme shown in FIGS. 8 and 9. In the present Example, the adapter molecule 300 shown in FIG. 7 was designed. The adapter molecule 300 designed in the present Example is, as shown in FIG. 8, a homo type adapter having a symmetrical structure which binds to the both ends of the double-stranded DNA to be analyzed. The adapter molecule 300 thus designed binds, by a ligation reaction, to the double-stranded DNA to be analyzed and becomes a bio-adapter molecule complex 305 having a symmetrical Y-shaped structure at both ends thereof. In the present Example, after preparation of the bio-adapter molecule complex 305, the primer 307 for sequencing is hybridized with the primer binding site 303. Next, when the bio-adapter molecule complex 305 and the polymerase are poured together in the first liquid tank 104A, the single-stranded nucleic acid region 301B which is in the form of a single strand only in one place in a library is drawn into the nanopore 101 by electrophoresis. As the double-stranded DNA passes through the nanopore 101, it is detached (unziped). When the DNA polymerase (molecular motor 306) bound to the molecular motor binding site 302 reaches the nanopore 101, the terminal portion of the primer 307 and the DNA polymerase which have been separated with the spacer 304 therebetween are brought into contact with each other to start a complementary strand synthesis reaction in the direction from the 5' end to the 3' end.

In the present Example, a predetermined region derived from a λ phage was used as the double-stranded DNA (the biomolecule 109) to be analyzed (SEQ ID NO: 1). The double-stranded DNA having a base sequence represented by SEQ ID NO: 1 can be obtained by PCR using a forward primer having a base sequence of from 1st to 21st bases in SEQ ID NO: 1 and a reverse primer having a reverse strand sequence of a base sequence of from 394th to 415th bases in SEQ ID NO: 1, with the genome of the λ phage as a template.

In the present Example, the adapter molecule 300 was prepared by synthesizing HomoAdaptor-template (SEQ ID NO: 2) and HomoAdaptor-primer (SEQ ID NO: 3) and hybridizing their complementary strand regions with each other. In SEQ ID NO: 2, 1st to 30th bases from the 5' end constitute one of the strands of the double-stranded nucleic acid region 112; 61st to 64th bases NNNN correspond to the spacer 304; and 65th to 91st bases correspond to the primer binding site 303. Further, 62nd to 92nd bases from the 5' end in SEQ ID No: 3 constitute the other strand of the double-stranded nucleic acid region 112. Still further, in the present Example, Sequencing Primer (SEQ ID NO: 4) was designed as the primer 307 to be hybridized with the primer binding site 303.

The phosphoric acid site at the 5' end of the HomoAdaptor-template and the dT site protruded from the 3' end of the HomoAdaptor-primer in the adaptor molecule 300 are hybridized with a dA-added PCR product. Since phosphorylation necessary for ligation is conducted, they are bound to the product (T/A ligation). It is designed that an adapter dimer is not formed at this time due to the presence of the protruding base in the adapter molecule 300.

Figure 11:
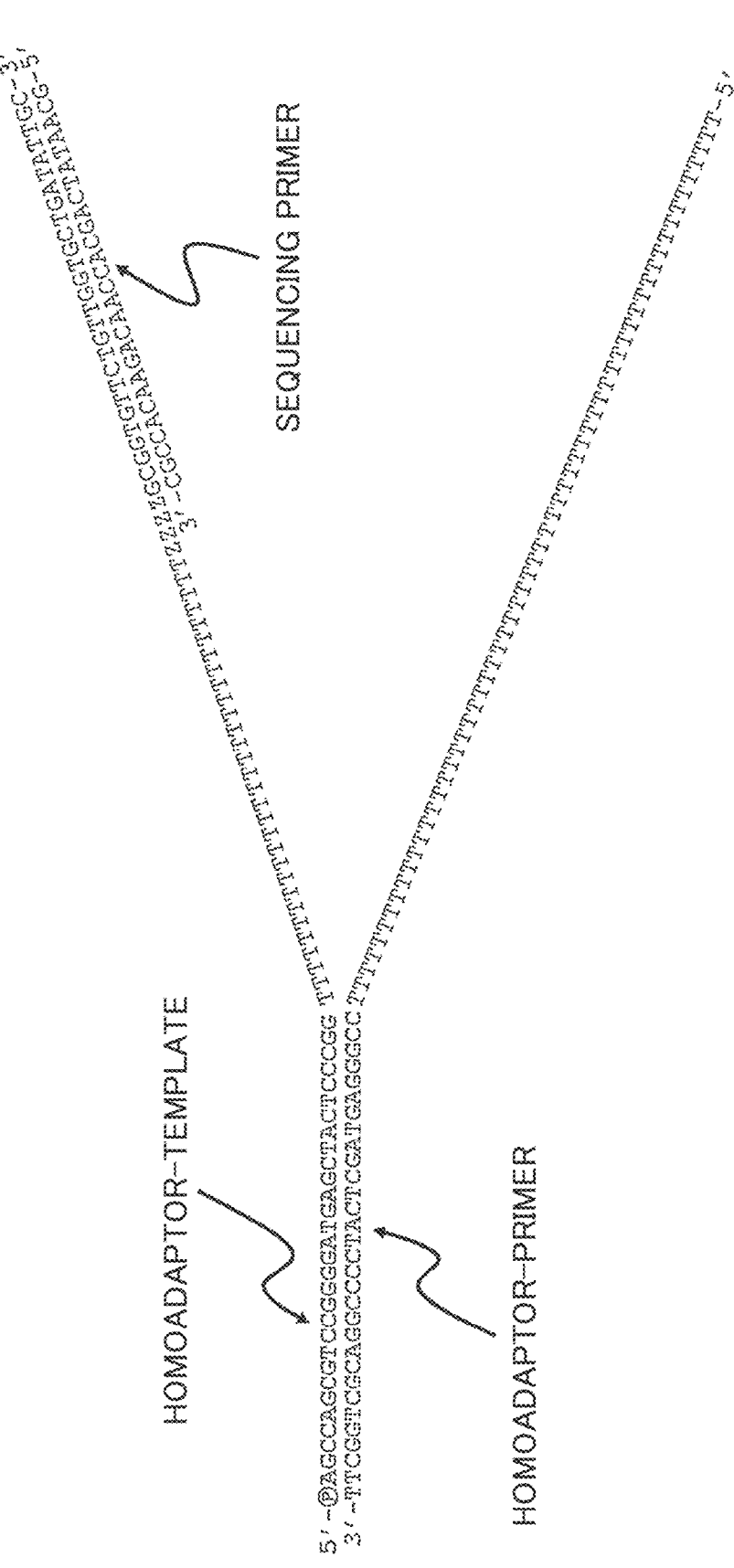
FIG. 11 is a diagram schematically showing the base sequence and the secondary structure of an adapter molecule designed in the present Example.

Specifically, a library was created by the following steps (refer to FIGS. 10 and 11).

(1) An adapter molecule 300 was prepared by (dissociating) the HomoAdaptor-template and the HomoAdaptor-primer at 80° C. for 10 minutes in Isothermal Buffer II and then, hybridizing them at 30° C. for 30 minutes (hybridization).

(2) The PCR-amplified DNA sample was subjected to end repair and dA addition treatments by conducting (an enzymatic reaction) at 20° C. for 30 minutes and then, (enzyme inactivation) at 65° C. for 30 minutes with an NEBNext® Ultra II End Repair/dA-Tailing Module, followed by purification with AMPure® XP.

(3) The adapter prepared in (1) was mixed with the dA added DNA sample prepared in (2) and T/A ligation was performed at room temperature (25° C.) for 30 minutes with Blunt/TA Ligase Master Mix. After the product was allowed to stand on ice, it was purified with AMPure® XP (an adapter: sample molar ratio was adjusted to 3:1).

(4) The sample ligated in (3) was hybridized with a Sequencing Primer in an Isothermal Buffer II at 30° C. for 30 minutes to prepare a final library.

The composition and the like of the reaction solution used in (1) to (4) are shown in FIG. 10. FIG. 11 schematically shows the base sequence and the secondary structure of the adapter molecule designed in the present Example.

Figure 12:
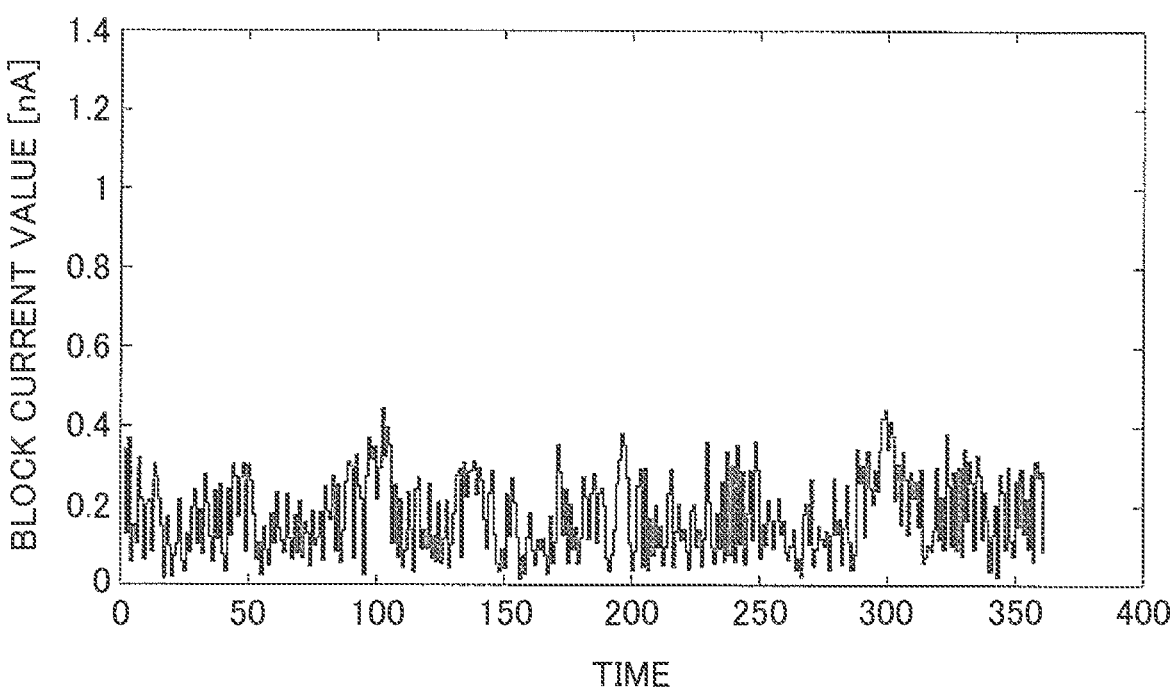
FIG. 12 is a characteristic diagram showing the standardization results of a block current value measured in the present Example.

The library thus obtained was subjected to electrophoresis with an electrophoresis apparatus (Tapestation 4200, product of Agilent technologies), the band analysis of it was conducted. In the present Example, a block current value measured was standardized (FIG. 12) and a correlation with an estimated block current value was studied. The correlation coefficient R2 was found to be 0.807. The results have suggested that using the adapter molecule 300 prepared in the present Example enables sequencing based on the aforesaid protocol not including a step of thermally modifying a double-stranded DNA into a single-stranded DNA.

The invention claimed is:

1. A method of analyzing a biomolecule, comprising:

a step of applying a voltage to between a first liquid tank and a second liquid tank, which are placed opposite to each other via a thin film having a nanopore, while filling the first liquid tank with an electrolyte solution containing a bio-adapter molecule complex and filling the second liquid tank with an electrolyte solution to form a potential gradient between the first liquid tank and the second liquid tank with the first liquid tank as a negative or ground potential and the second liquid tank as a positive potential; and a step of measuring a signal generated when the bio-adapter molecule complex passes through the nanopore from the second liquid tank to the first liquid tank;

wherein in the step of forming a potential gradient, a single-stranded nucleic acid region of the bio-adapter molecule complex is introduced into the second liquid tank via the nanopore and the bio-adapter molecule complex transfers from the first liquid tank to the second liquid tank by the potential gradient formed between the first liquid tank and the second liquid tank, wherein the bio-adapter molecule complex has a molecular motor binding site in a single-stranded nucleic acid region having a 3' end as a terminal portion thereof and has a primer binding site on the side of the 3' end relative to the molecular motor binding site, the electrolyte solution with which the first liquid tank is filled contains a molecular motor which can bind to the molecular motor binding site, the bio-adapter molecule complex has a spacer to which the molecular motor cannot be bound between the molecular motor binding site and the primer binding site, the bio-adapter molecule complex has a first block molecule having a diameter larger than the diameter of the nanopore placed in a single-stranded nucleic acid region having a 3' end as a terminal portion thereof, a second block molecule having a diameter smaller than the diameter of the nanopore binds to a 5' end of the single-stranded nucleic acid region, the single-stranded nucleic acid region having the 5' end is introduced into the second liquid tank, and the first block molecule placed in the single-stranded nucleic acid region having the 3' end having the molecular motor binding site is brought into contact with the nanopore to stop the transfer of the bio-adapter molecule complex from the first liquid tank to the second liquid tank.

2. The method of analyzing a biomolecule according to claim 1, wherein the single-stranded nucleic acid region having the 5' end as a terminal portion thereof is introduced into the second liquid tank via the nanopore.

3. The method of analyzing a biomolecule according to claim 1, wherein the molecular motor binds to the molecular motor binding site and the molecular motor transfers the bio-adapter molecule complex from the second liquid tank to the first liquid tank.

4. The method of analyzing a biomolecule according to claim 1, wherein the electrolyte solution with which the first liquid tank is filled contains a primer which can be hybridized with the primer binding site, and the molecular motor synthesizes a complementary strand from the primer hybridized with the primer binding site and thereby transfers the bio-adapter molecule complex from the second liquid tank to the first liquid tank.

5. The method of analyzing a biomolecule according to claim 1, wherein the molecular motor in contact with the nanopore synthesizes a complementary strand from the primer hybridized with the primer binding site and thereby transfers the bio-adapter molecule complex from the second liquid tank to the first liquid tank.

6. The method of analyzing a biomolecule according to claim 1, wherein in the step of measuring a signal, a voltage applied to between the first liquid tank and the second liquid tank is reversed when a signal from a specific region of the adapter molecule is measured and a potential gradient is formed with the first liquid tank as a positive potential and with the second liquid tank as a negative or ground potential.

7. The method of analyzing a biomolecule according to claim 1, wherein the second block molecule that binds to the 5' end of the single-stranded nucleic acid region is introduced into the second liquid tank via the nanopore. 5

8. The method of analyzing a biomolecule according to claim 1, wherein the step of measuring a signal is repeated by controlling a voltage to be applied to between the first liquid tank and the second liquid tank and thereby reciprocating the bio-adapter molecule complex between the first 10 liquid tank and the second liquid tank.

9. The method of analyzing a biomolecule according to claim 1, wherein the first block molecule and the second block molecule are selected from avidin, streptavidin, or a complex between an anti-DIG antibody and a bead. 15

\*  \*  \*  \*  \*

SEQUENCE LISTING

```
<160> NUMBER OF SEQ ID NOS: 4

<210> SEQ ID NO 1
<211> LENGTH: 415
<212> TYPE: DNA
<213> ORGANISM: Coliphage lambda

<400> SEQUENCE: 1
gagcaaagca aaacaggcgt aaaaattgcc atcccaacag cattgcatat tgatgctctc        60
ggaatatcaa tgaaggaaac acttgataaa tgcaaagaga ttcttggcgg agaaaccata       120
attgcatcta ctcgtcgcga accgctttca tccggcacag tatcaaggta ttttatgcgc       180
gcacgaaaag catcaggtct ttccttcgaa ggggatccgc ctacctttca cgagttgcgc       240
agtttgtctg caagactcta tgagaagcag ataagcgata agtttgctca acatcttctc       300
gggcataagt cggacaccat ggcatcacag tatcgtgatg acagaggcag ggagtgggac       360
aaaattgaaa tcaaataatg attttatttt gactgatagt gacctgttcg ttgca           415

<210> SEQ ID NO 2
<211> LENGTH: 87
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (60)..(61)
<223> OTHER INFORMATION: spacer between residues 60 and 61, not binding
      a molecular motor

<400> SEQUENCE: 2
agccagcgtc cggggatgag ctactcccgg tttttttttt tttttttttt tttttttttt        60
gcggtgttct gttggtgctg atattgc                                           87
```

```
<210> SEQ ID NO 3
<211> LENGTH: 92
<212> TYPE: DNA
<213> ORGANISM: Artificial Sequence
<220> FEATURE:
<223> OTHER INFORMATION: Synthetic DNA

<400> SEQUENCE: 3
tttttttttt tttttttttt tttttttttt tttttttttt tttttttttt tttttttttt        60
tccgggagta gctcatcccc ggacgctggc tt                                       92

<210> SEQ ID NO 4
<211> LENGTH: 27
<212> TYPE: DNA
<213> ORGANISM: Artificial Sequence
<220> FEATURE:
<223> OTHER INFORMATION: Synthetic DNA

<400> SEQUENCE: 4
gcaatatcag caccaacaga acaccgc                                             27
```